US012350473B2

(12) United States Patent
Flather et al.

(10) Patent No.: US 12,350,473 B2
(45) Date of Patent: *Jul. 8, 2025

(54) EMERGENCY DEVICES

(71) Applicant: ZMI Pharma Inc., San Diego, CA (US)

(72) Inventors: Mark J. Flather, San Diego, CA (US); Karen K. Daniels, San Diego, CA (US); Thomas Moll, San Diego, CA (US); Ronald B. Moss, San Diego, CA (US); Dennis J. Carlo, San Diego, CA (US)

(73) Assignee: ZMI Pharma Inc., San Diego, CA (US)

(*) Notice: Subject to any disclaimer, the term of this patent is extended or adjusted under 35 U.S.C. 154(b) by 193 days.

This patent is subject to a terminal disclaimer.

(21) Appl. No.: 17/340,977

(22) Filed: Jun. 7, 2021

(65) Prior Publication Data

US 2021/0290857 A1   Sep. 23, 2021

Related U.S. Application Data

(63) Continuation of application No. 16/592,319, filed on Oct. 3, 2019, now Pat. No. 11,027,072, which is a continuation-in-part of application No. 16/422,639, filed on May 24, 2019, now Pat. No. 11,571,518.

(60) Provisional application No. 62/747,007, filed on Oct. 17, 2018, provisional application No. 62/676,742, filed on May 25, 2018.

(51) Int. Cl.
*A61M 5/315*    (2006.01)
*A61K 31/485*   (2006.01)
*A61M 5/32*     (2006.01)

(52) U.S. Cl.
CPC ....... *A61M 5/31535* (2013.01); *A61K 31/485* (2013.01); *A61M 5/31591* (2013.01); *A61M 5/3202* (2013.01); *A61M 2209/06* (2013.01)

(58) Field of Classification Search
CPC .................... A61M 5/31535; A61K 31/485
See application file for complete search history.

(56) References Cited

U.S. PATENT DOCUMENTS

| | | | |
|---|---|---|---|
| 4,267,846 A | 5/1981 | Kontos | |
| 5,281,198 A | 1/1994 | Haber et al. | |
| 5,358,489 A | 10/1994 | Wyrick | |
| 5,713,866 A | 2/1998 | Wilmot | |
| 5,743,887 A | 4/1998 | Brattesani | |
| 6,616,634 B2 | 9/2003 | Benz et al. | |
| 8,627,816 B2 | 1/2014 | Edwards et al. | |
| 9,144,648 B2 | 9/2015 | Lesch, Jr. et al. | |
| 9,517,307 B2* | 12/2016 | Blondino | A61M 5/2053 |
| 11,027,072 B2* | 6/2021 | Flather | A61M 5/31535 |
| 11,141,540 B2 | 10/2021 | Rolfs et al. | |
| 11,571,518 B2* | 2/2023 | Flather | A61M 5/20 |
| 2005/0101919 A1 | 5/2005 | Brunnberg | |
| 2005/0261634 A1 | 11/2005 | Karlsson | |
| 2005/0273054 A1 | 12/2005 | Asch | |
| 2007/0017533 A1 | 1/2007 | Wyrick | |
| 2008/0103435 A1 | 5/2008 | Graf et al. | |
| 2008/0234634 A1 | 9/2008 | Eiland et al. | |
| 2012/0217184 A1 | 8/2012 | Edwards et al. | |
| 2013/0204229 A1 | 8/2013 | Olson et al. | |
| 2015/0051580 A1 | 2/2015 | Shain et al. | |
| 2015/0165129 A1 | 6/2015 | Row et al. | |
| 2016/0184521 A1 | 6/2016 | Edwards et al. | |
| 2019/0358403 A1 | 11/2019 | Flather et al. | |
| 2022/0023547 A1 | 1/2022 | Rolfs et al. | |

FOREIGN PATENT DOCUMENTS

| | | |
|---|---|---|
| AU | 2012209222 B2 | 2/2012 |
| EP | 2687251 A1 | 1/2014 |
| EP | 2874683 B1 | 1/2021 |
| SU | 1727846 A1 | 4/1992 |
| WO | 2011/049713 A2 | 4/2011 |
| WO | 2012/148717 A1 | 11/2012 |
| WO | 2013/071138 A1 | 5/2013 |
| WO | 2013/153121 A2 | 10/2013 |
| WO | 2014/162551 A1 | 10/2014 |
| WO | 2017/034618 A1 | 3/2017 |
| WO | 2019/227061 A1 | 11/2019 |

OTHER PUBLICATIONS

International Search Report and Written Opinion mailed on Jun. 13, 2016, for International Application Serial No. PCT/US2016/022956 filed on Mar. 17, 2016.
Krieter et al., Pharmacokinetic properties and human use characteristics of an FDA-approved intranasal naloxone product for the treatment of opioid overdose. The Journal of Clinical Pharmacology, vol. 56, No. 10, pp. 1243-1253 (2016).
International Search Report and Written Opinion, dated Aug. 2, 2019, for International Application No. PCT/US2019/034028 filed May 24, 2019.
Extended European Search Report, dated Feb. 4, 2022, for European Patent Application No. 19808355.2.

* cited by examiner

*Primary Examiner* — Kevin E Weddington
(74) *Attorney, Agent, or Firm* — Greenberg Traurig, LLP

(57) ABSTRACT

Described herein are syringe devices comprising a syringe including a therapeutic dose of at least one drug to be used in a drug or substance overdose. Also provided herein are compositions and methods of treating opioid overdose using high dose naloxone.

15 Claims, 12 Drawing Sheets

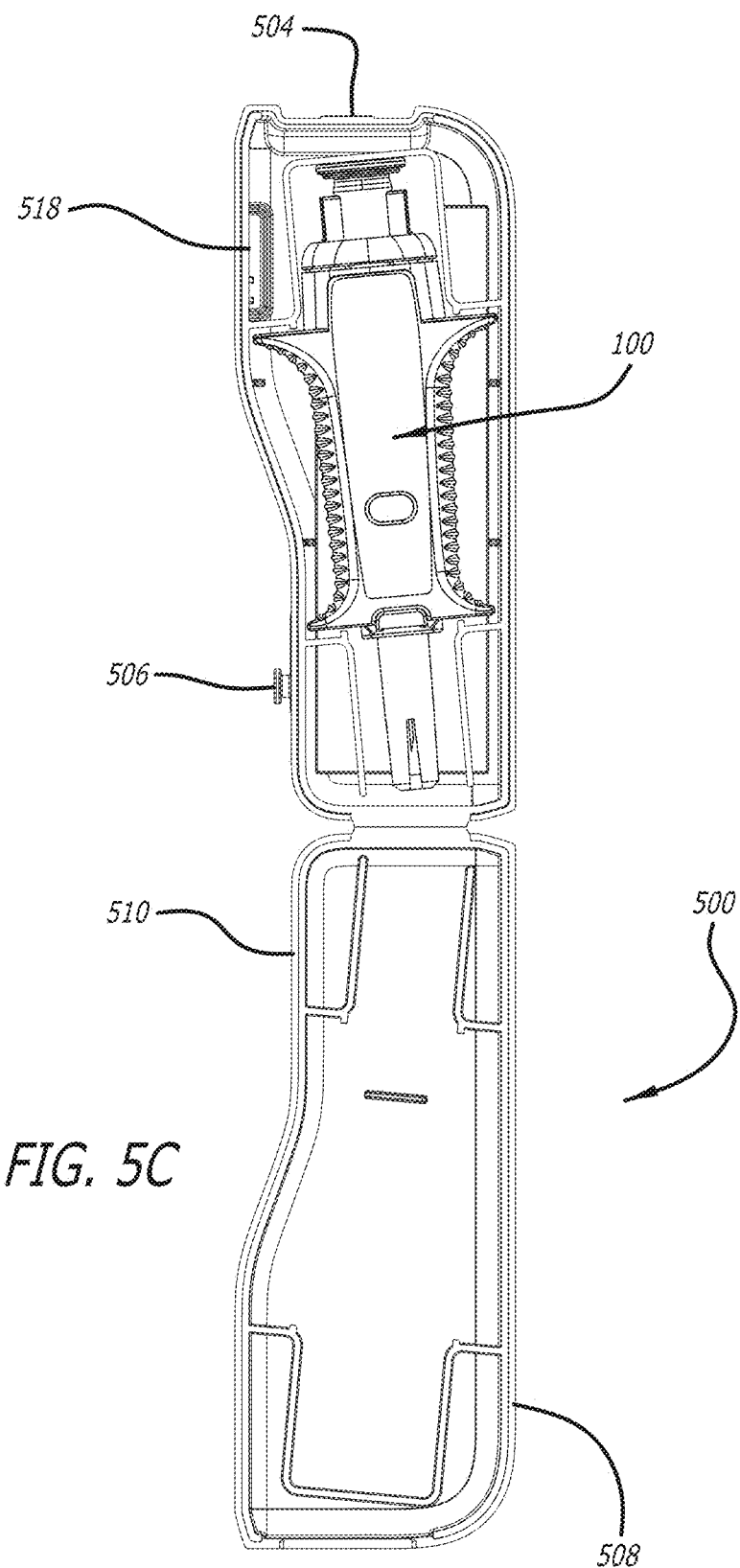

EMERGENCY DEVICES

CROSS REFERENCE TO RELATED APPLICATIONS

This application is a continuation of U.S. patent application Ser. No. 16/592,319, filed Oct. 3, 2019, which is a continuation-in-part of U.S. patent application Ser. No. 16/422,639, filed May 24, 2019, which claims the benefit of U.S. Provisional Patent Application No. 62/676,742, filed May 25, 2018, the entire disclosures of which are incorporated herein by reference.

This application claims the benefit of U.S. Provisional Patent Application No. 62/747,007, filed Oct. 17, 2018, the entire disclosure of which is incorporated herein by reference.

FIELD

The present invention relates generally to syringes, encasements for syringes, devices including syringes, and methods of using same for emergencies. Also described are compositions and methods of treating opioid overdose using naloxone with the syringe devices as described herein.

SUMMARY

Described herein generally are syringe devices that can deliver a therapeutic dose of a pharmaceutical agent used to treat a drug or substance overdose. In some embodiments, the therapeutic dose can be less than the amount of pharmaceutical agent in the syringe. The devices can also prevent device tampering by a user and/or multiple uses of the same syringe device. In some embodiments, the syringe devices described herein can be used in a critical situation for delivery of an emergency and/or time sensitive pharmaceutical agent in response to a drug or substance overdose. The syringe devices can include a syringe that includes a dose of at least one pharmaceutical agent and can deliver a therapeutic dose of the pharmaceutical agent that can be less than the amount of pharmaceutical agent in the syringe. The syringe can also include a stopper and a gas bubble between the at least one pharmaceutical agent and the stopper. In other embodiments, a gas bubble is not needed and/or desired.

The syringe devices can include an encasement to house the syringe and plunger assembly including a plunger rod, an actuator, and a spacer. In some embodiments, when assembled, the syringe devices can prevent users from tampering with the encased syringe and/or using it for more than one pharmaceutical agent delivery. In some embodiments, the syringe devices can be single use and lock after use.

In various embodiments, the actuator and the spacer can be configured to be secured around the plunger rod. The actuator can include channels and the plunger rod can include protrusions, and the protrusions can be configured to fit within the channels and can provide an adjustable plunger rod location without moving a force application surface.

In some embodiments, the actuator itself can include a finger depression location at the syringe device's force application location instead of force being applied to the plunger rod as in conventional syringes.

The plunger assembly, in some embodiments, can be configured to move the stopper a predetermined distance without a user touching the plunger rod or being able to retract the plunger rod.

In some embodiments, the encasement can be a rigid plastic casing and can include a window configured to allow a user to view the at least one pharmaceutical agent in the syringe to determine if the at least one pharmaceutical agent has or has not expired. A user can tell from potential cloudiness or discoloration if the at least one pharmaceutical agent has expired.

In other embodiments, the encasement can include a needle guard configured to allow the user to cover the needle after use. In such embodiments, the needle guard can slide down from the encasement over the exposed needle to protect from accidental needle sticks after use.

The at least one pharmaceutical agent can be any pharmaceutical agent or combination of pharmaceutical agents described herein. In some embodiments, the pharmaceutical agent(s) can be ones that might be used in an emergency situation to treat a drug or substance overdose. Such pharmaceutical agents can include, but are not limited to naloxone. In some embodiments, a therapeutic amount of these pharmaceutical agents can be about 1 mg to about 100 mg.

Embodiments include syringe devices including a syringe comprising a volume of at least one pharmaceutical agent and a stopper; a plunger assembly including a plunger rod, an actuator, and a spacer. These syringe devices' plunger assemblies can be configured to provide substantially identical doses of the at least one pharmaceutical agent even if more or less pharmaceutical agent is provided in the syringe by moving the stopper a predetermined distance. The volume of the pharmaceutical agent in the syringe can be at least about 0.5 cc.

Also described herein are methods for using the herein-described syringe devices to deliver a pharmaceutical agent (s). Some methods can be for administering a therapeutic dose of at least one pharmaceutical agent. In some embodiments, the administering can be in an emergency to treat a drug or substance overdose. The methods can include advancing a stopper through a syringe including the therapeutic dose of the at least one pharmaceutical agent thereby delivering it to a patient in need thereof.

This advancing can be a predetermined distance. In various embodiments, advancing the stopper the predetermined distance allows a particular amount of pharmaceutical agent to be extruded and/or ejected from the syringe device, for example, through a needle. In some embodiments, the advancing can be configured to deliver about 1 mg to about 100 mg of the at least one pharmaceutical agent to a user and/or patient. Other amounts of pharmaceutical agent can be delivered in other embodiments.

In some embodiments, the actuator and the spacer may be configured to be secured around the plunger rod and provide the predetermined distance between a start point and an end point on the spacer.

Also, provided herein are compositions and methods of treating opioid overdose using naloxone.

In some embodiments, the compositions can be administered by injection. In some embodiments, the injection can be intramuscular. In other embodiments, the compositions can be a high dose of naloxone. In other embodiments, the compositions can be administered by the syringe devices described herein.

BRIEF DESCRIPTION OF THE DRAWINGS

FIG. 5C illustrates a top view of a case for the syringe devices described herein in an open configuration including a syringe device loaded therein.

DETAILED DESCRIPTION

Figure 1:
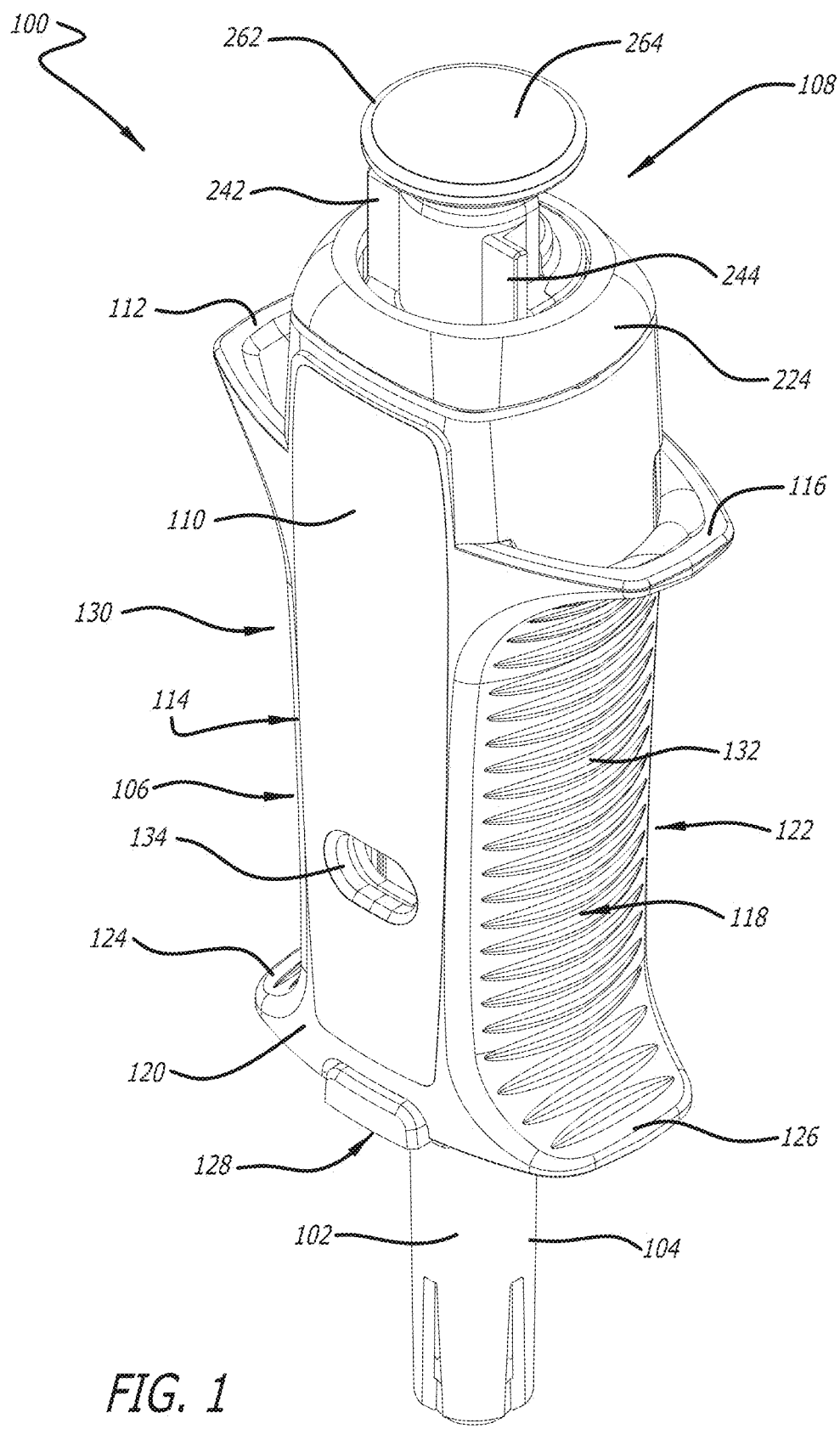
FIG. 1 illustrates a perspective view of a syringe device as described herein.

Described herein generally are syringe devices that allow accurate dosing of a pharmaceutical agent(s), even in situations that require immediate and sometimes rushed interventions in response to a drug or substance overdose. In some embodiments, these situations can be emergency situations where a drug or substance overdose has occurred and time is of the essence.

The syringe devices and/or any accompanying packaging or casing can be sized to be small enough to be portable and/or easily stored. In some embodiments, small size can allow end users to more easily carry the syringe devices and have them available in an emergency situation. In some embodiments, the syringe devices can be stocked in emergency rooms and with emergency medical personnel. Other first responders can also be supplied with syringe devices as described herein. Emergency medical kits can include a syringe device or a syringe device can be deployed when responding to a situation with a drug or substance overdose.

In some embodiments, syringe devices can be supplied at locations where drug and/or substance abuse is likely to occur. For example, syringe devices can be supplied at concerts, parties, clinics, homeless shelters, halfway houses, sober living facilities, and the like.

The syringe devices described herein can allow for current manufacturing tolerances without affecting delivered volume accuracy as will be described herein. A controlled tolerance loop can be used for a delivery stroke in combination with an adjustable plunger rod at the point of secondary packaging. In other words, in some embodiments, volume delivery accuracy does not change if more or less pharmaceutical agent is delivered in a syringe prior to assembly of the syringe device.

Further, features of the syringe devices can prevent outward movement of a plunger rod/stopper under all conditions by means of a mechanical stop. A mechanical stop can prevent outward movement that can introduce air into a needle and/or a syringe that can prevent introduction of a pharmaceutical agent during an emergency drug or substance overdose. The syringe devices can also include a removable locking mechanism. The locking mechanism can be removed prior to use. This removable locking mechanism can prevent inward movement of the plunger rod/stopper up to the point of use.

The syringe devices can also provide tactile feedback to a user at the end of a stroke. This tactile feedback can be useful to inform the user that a dose has been delivered.

Further, the syringe devices can include a locking feature that locks the plunger rod down at the stroke end to assure gas bubble decompression and accurate delivered volume. In some embodiments, a gas bubble is not included and no gas bubble compression exists at the end of a plunger stroke.

The syringe devices can encase a pharmaceutical agent filled syringe such that an end user cannot unscrew or over screw the plunger rod from the stopper and change the travel stroke and thus delivered volume. In some embodiments, a user would have to physically break open the syringe device in order to alter pharmaceutical agent delivery.

Figure 2:
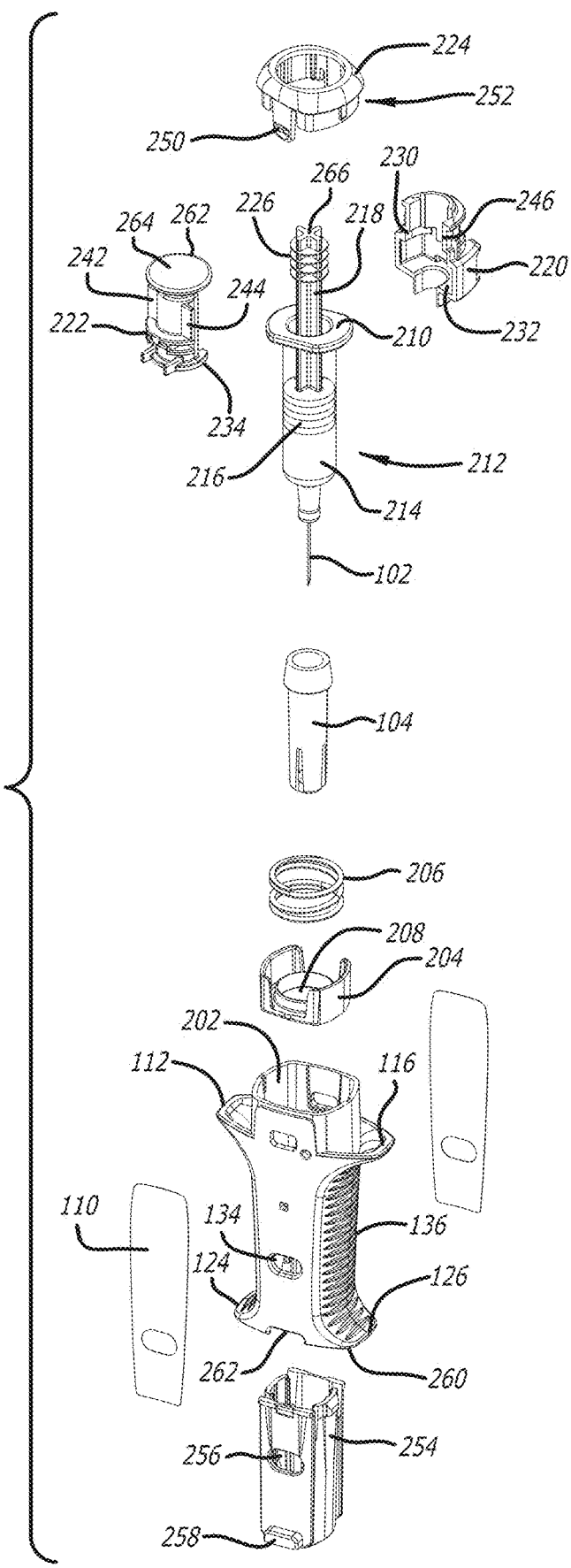
FIG. 2 is an exploded view of the syringe device of FIG. 1.
Figure 3A:
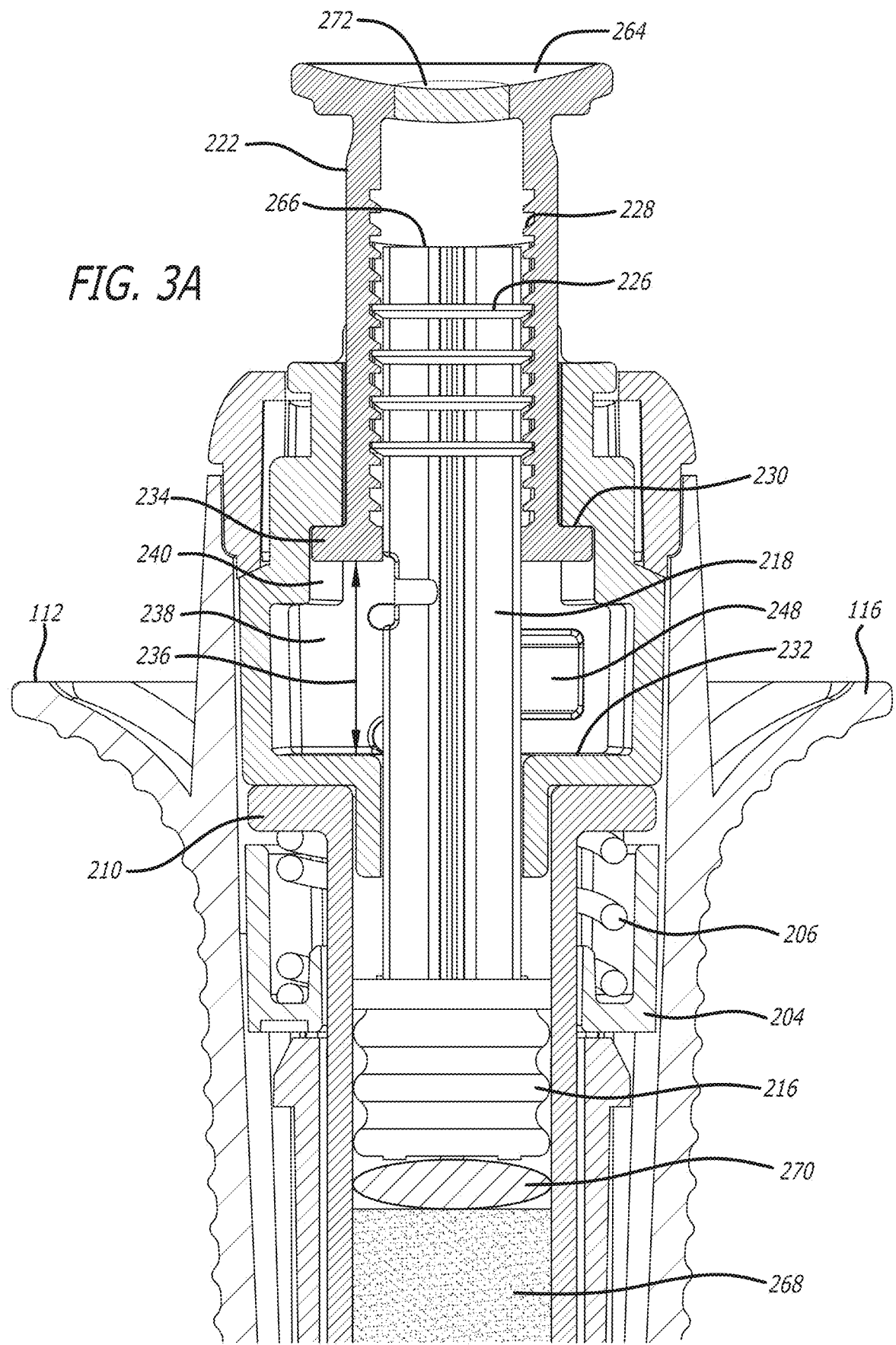
FIG. 3A illustrates a cross-sectional view of the syringe of FIG. 1 with a pharmaceutical agent in the syringe.
Figure 3B:
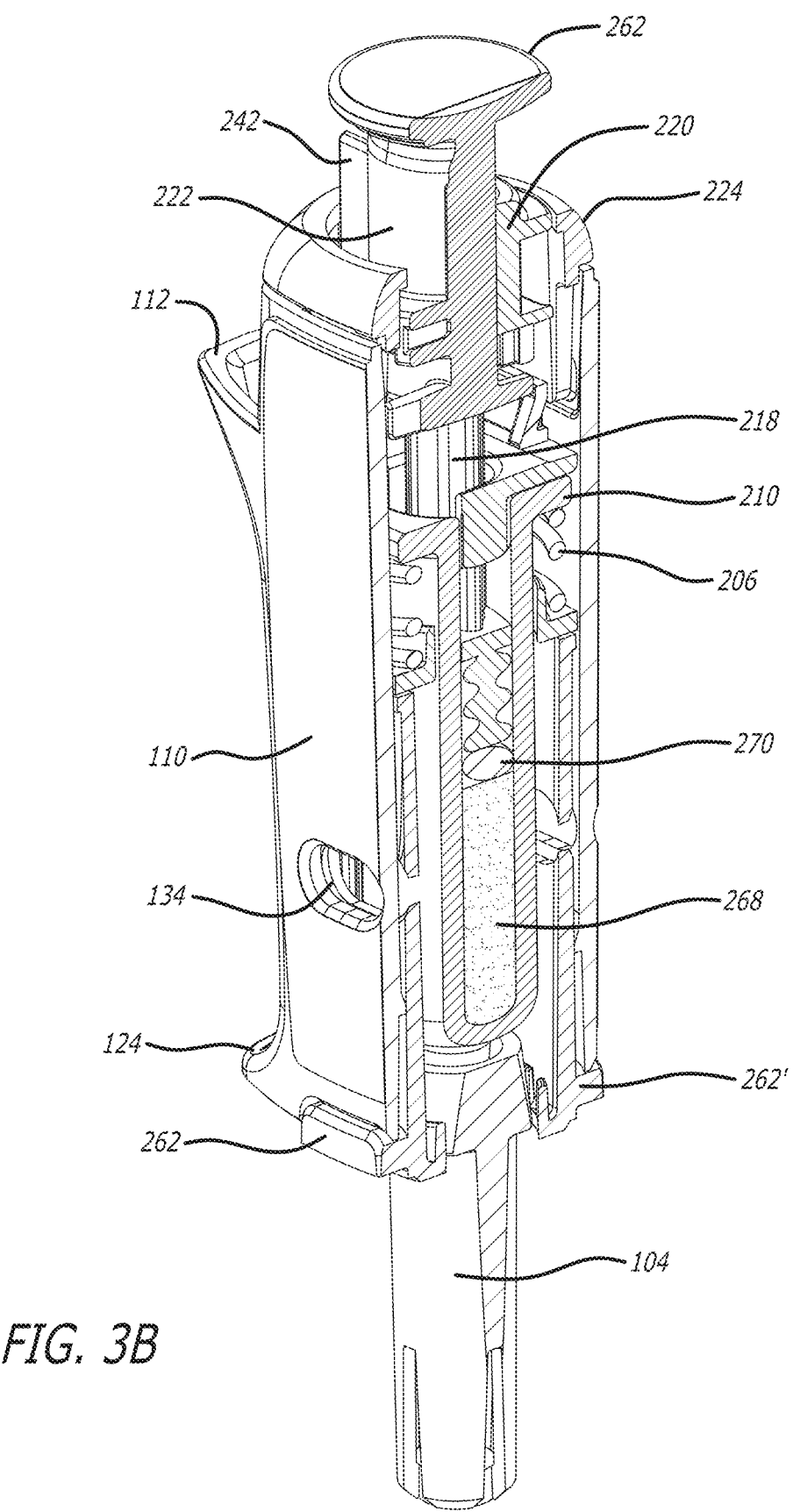
FIG. 3B illustrates another cross-sectional view of the syringe of FIG. 1.

A syringe device can be as illustrated in FIG. 1. FIG. 2 illustrates a cross-section thereof and FIGS. 3A-C illustrate various cross-sections thereof. Syringe device 100 can include a needle 102, a needle guard 104, an encasement 106, and a plunger assembly 108. Encasement 106 and plunger assembly 108 can include many features that will be described in more detail herein.

Encasement 106 can include one or more labels that provide information about the pharmaceutical agent(s) being delivered via syringe device 100. As illustrated in FIG. 1, label 110 can cover substantially an entire surface of encasement 106. However, in other embodiments, label 110 may not cover an entire surface of encasement 106 or multiple labels can be used instead of one large label. In fact, in some embodiments, any number of labels of any shapes can be used to label the product as needed.

Encasement 106 can include any number of flanges. Upper flanges can provide counter balance locations to apply force during injection. Encasement 106 includes a first upper flange 112 on first side 114 and second upper flange 116 on second side 118. Encasement 106 can, in other embodiments, include an upper flange that wraps around the entire perimeter or a substantial portion of the perimeter of encasement 106. However, in the embodiment illustrated in FIG. 1, first upper flange 112 and second upper flange 116 are not on the entire perimeter of top surface 120 of encasement 106 in order to reduce the size of syringe device 100.

Encasement 106 can also include a first lower flange 124 on first side 114 and second lower flange 126 on second side 118. Again, encasement 106 can, in other embodiments, include a lower flange that wraps around the entire perimeter or a substantial portion of perimeter of encasement 106. However, in the embodiment illustrated in FIG. 1, first lower flange 124 and second lower flange 126 are not on the entire perimeter of bottom surface 122 of encasement 106 in order to reduce the size of syringe device 100, In one embodiment, first lower flange 124 and second lower flange 126 create a bottom surface 128. Bottom surface 128, first lower flange 124, and second lower flange 126 can aid with needle insertion by providing a push point. Further, bottom surface 128 with a large surface area provided by the flanges can promote correct orientation with respect to the skin for maximum needle penetration depth.

One or more areas or portions on the face of encasement 106 can include gripping surfaces. Gripping surfaces can include those with textures, perforations, holes, or any other structures that promote grip of syringe device 100. In one embodiment, a gripping surface can be horizontal lines of raised surface. In some embodiments, a gripping surface can be molded into an encasement, and in other embodiments, a gripping surface can be coated in a surface with a high degree of friction, such as rubber. Gripping surfaces or gripping areas can promote easy grasping of syringe device 100 and promote many different syringe holding styles. In one embodiment, a first grip area 130 can exist between first upper flange 112 and first lower flange 124 and a second grip area 132 can exist between second upper flange 116 and second lower flange 126.

Encasement 106 can also include one or more indicia of pharmaceutical agent effectiveness. Indicia can include temperature color change labels that indicate whether the syringe has been subjected to suboptimal temperatures, one or more windows that allow a user to view the pharmaceutical agent within a syringe located within encasement 106, and/or a seal that can be broken prior to use to alert a user whether the syringe had previously been tampered with. In some embodiments, encasement 106 has one or more windows through first side 114, second side 118, or both. In one embodiment, encasement 106 includes a first window 134 on first side 114 and a second window 136 on second side 118. First window 134 and second window 136 can allow a user to view the pharmaceutical agent housed within encasement 106 to see, for example, if a clear solution may be cloudy and hence expired.

An exploded view of syringe device 100 is illustrated in FIG. 2. Within encasement 106 resides several of the syringe device's components. Loaded from distal end 202 of encasement 106 is a syringe stop ring 204 that allows a spring 206 to rest within. Syringe stop ring 204 includes a hole 208 through its body through which a needle 102 and syringe body is inserted through. Spring 206 can rest between syringe stop ring 204 and flange 210 of syringe 212. This arrangement is illustrated in cross-sectional FIGS. 3A and 3B. In some embodiments, syringe flange 210 can be held against spacer 220 by spring 206. If during force of actuation, there is a separation between spacer 220 and syringe flange 210, spring 206 can close this separation after user applied force is removed.

Syringe 212 can include an internal volume 214 that can be filled with one or more pharmaceutical agents. Pharmaceutical agents can be extruded and/or ejected from needle 102 by applying force to stopper 216 by plunger rod 218. Plunger rod 218 can come bonded to stopper 216 or can be screwed into or otherwise attached to stopper using any means known in the art.

Plunger rod 218 is part of plunger assembly 108. Plunger assembly 108 includes plunger rod 218, spacer 220, actuator 222, and top 224. Plunger rod 218 can include multiple protrusions 226 that can interact with channels 228 within inner surface of actuator 222. Protrusions 226 can lock actuator 222 to plunger rod 218.

Spacer 220 is used as a top stop 230 and a bottom stop 232 for actuator ring 234. Top and bottom stops control the amount of stopper travel through syringe 212 and hence the precise amount of pharmaceutical agent extruded and/or ejected from needle 102. Distance 236 can be defined between top stop 230 and bottom stop 232. Distance 236 can be about 4 mm, about 5 mm, about 6 mm, about 7 mm, about 8 mm, about 9 mm, about 10 mm, about 12 mm, about 14 mm, about 16 mm, about 18 mm, about 20 mm, about 22 mm, about 24 mm, between about 1 mm and about 24 mm, between about 4 mm and about 14 mm, or between about 10 mm and about 24 mm.

Distance 236 includes travel distance through spacer cavity 238 and distance through spacer cavity bore 240. Spacer cavity bore 240 includes a partial internal diameter that fits the outer partial diameter of actuator ring 234. In some embodiments, spacer cavity 238 includes an internal diameter that is larger than the outer partial diameter of actuator ring 234. Thus, in some embodiments, when actuator ring 234 is advanced out of spacer cavity bore 240 into spacer cavity 238, it encounters an area where actuator ring 234 is not guided by the fit in spacer cavity bore 240. In order to account for the travel through spacer cavity 238, actuator 222 includes at least one guide rail to prevent rotation(s) and/or alignment issues when advancing actuator 222. In one embodiment, actuator 222 includes first guide rail 242 and second guide rail 244. First guide rail 242 and second guide rail 244 travel against front face 246 of spacer 220.

In some embodiments, distance 236 can be changed, for example reduced, by increasing the thickness of actuator ring 234. Likewise, distance 236 can be increased by reducing the thickness of actuator ring 236. By increasing the thickness of an actuator ring, the amount of distance traveled between top stop 230 and bottom stop 232 can be reduced resulting in less volume of pharmaceutical agent being extruded and/or ejected from needle 102. Such reduced travel distances can be used with smaller patients that require less pharmaceutical agent to treat a particular symptom of drug or substance overdose. For example, in some embodiments, in an emergency drug or substance overdose situation, the patient may have a thin or lightweight build from years of abuse.

In some embodiments, distance 236 can be changed by decreasing the distance between top stop 230 and bottom stop 232 without changing the thickness of actuator ring 234. By adjusting, e.g., increasing or decreasing, the distance between top stop 230 and bottom stop 232, the amount of distance traveled between top stop 230 and bottom stop 232 can be changed resulting in more or less volume of pharmaceutical agent being extruded from needle 102.

In embodiments, distance 236 can be changed by combinations of adjusting the thickness of actuator ring 234 and adjusting the distance between top stop 230 and bottom stop 232.

Actuator 222 can be adjusted relative to plunger rod 218 based on filling variability. FIGS. 3A and 3B illustrate this. In other words, regardless of the volume of pharmaceutical agent in a particular syringe (and hence a location of stopper 216 relative to flange 210), actuator 222 and stopper 220 can be attached to plunger rod 218 and provide an accurate pharmaceutical agent volume delivery.

In one embodiment, if a syringe is provided with too much pharmaceutical agent volume, the actuator and the spacer can be attached around the plunger rod such that protrusions 226 are at a higher location in channels 228. In such an embodiment, the ultimate delivered volume would be the same as if the syringe was provided with less pharmaceutical agent volume.

This changeability of plunger assembly can allow variability in fill volume without having to change manufacturing processes to accommodate different and/or inaccurate fills. The changeability allows for a particular volume of pharmaceutical agent to be extruded and/or ejected from needle 102 regardless of the actual fill volume in the syringe.

In some embodiments, a snap 248 is located at bottom stop 232 to lock plunger rod 218 down via actuator ring 234 at the end of an injection stroke. This lock prevents attempted multiple uses of a syringe. In essence, the lock allows a syringe to be a single use, disposable syringe.

Top 224 includes a hole through it to allow the assembled plunger rod 218, spacer 220 and actuator 222 to protrude at least partially. Top 224 includes at least one tooth, such as first tooth 250 and second tooth 252 to snap into portions of encasement 106. After top 224 is locked into encasement 106, it acts to lock spacer 220 into place by wedging spacer 220 between top 224 and syringe flange 210.

In some embodiments, spacer 220, actuator 222, and top 224 can be keyed to encasement 106 to prevent rotation of the components once assembled.

In some embodiments, syringe device 100 can include a needle guard 254. Needle guard 254 can be manually deployed. Needle guard 254 can include at least one hole 256 that can align with a window on encasement 106 when the needle guard has not been manually deployed. Needle guard 254 can be deployed to aid in injury prevention after use of syringe device 100.

Needle guard 254 can be manually deployed by applying pressure to and pulling on one or more tabs 258 away from proximal end 260 of encasement 106. Proximal end 260 includes indentations 262 to allow full retraction of needle guard 254 into encasement 106. Once fully deployed, needle guard 254 can lock into place preventing needle 102 from being used further or accidentally lancing a human handling the used syringe. This may be particularly important when treating a drug abuser that may have illness or disease acquired from the drug abuse, such as but not limited to HIV and AIDS.

In some embodiments, the needle guard can automatically retract after a dose of pharmaceutical agent has been delivered to a patient. As the user retracts the needle from the patient, needle guard 254 deploys from encasement 106. Deployment can be through a spring force unlocked when force is placed on proximal end 260 of encasement 106 during an injection. Thus, when pulling device 100 away from a patient's skin, needle guard 234 can deploy. In other embodiments, a button can be pressed to begin deploying needle guard 254. The button can simply release a spring force that snaps needle guard into place preventing an accidental needle stick.

Actuator 222 can further include a force application surface 262 at its distal end. Force application surface 262 can be a concave surface 264 promoting user comfort during actuation of the syringe devices. Further, in some embodiments, force application surface 262 can be textured to aid in user feeling when using the syringe devices.

In some embodiments, force application surface 262 can be transparent, such as including a window 272 provided by a material allowing a user to see the top of plunger rod 218. Window 272 can be through the entirety of force application surface 262, particularly at apex of concave surface 264 or otherwise in the center thereof.

The top of plunger rod 218 can include an indication surface 266. Indication surface 266 can be unique to the pharmaceutical agent included in device 100. In some embodiments, indication surface 266 can include raised features such as shapes or can include words or images applied to the surface.

This windowed configuration can prevent label tampering, because the indication surface 266 is internal to the device.

As further illustrated in FIGS. 3A and 3B, internal volume 214 includes a liquid pharmaceutical agent 268. Existing between liquid pharmaceutical agent 268 and stopper 216 can be a gas bubble 270. Gas bubble 270 can be virtually any gas that can occupy the space required between the liquid pharmaceutical agent and the stopper. In some embodiments, a gas bubble is not included.

In some embodiments, the liquid pharmaceutical agent may be substituted with a semisolid or gel pharmaceutical agent. In some embodiments, a pharmaceutical agent delivery vehicle can be used that can be extruded from the needle.

In some embodiments, the gas can be an inert gas such as, but not limited to, argon, nitrogen, helium, and the like. In one embodiment, the gas bubble is nitrogen. In some embodiments, the devices described herein do not include a gas bubble. In other embodiments, the gas bubble is not needed as the end of a plunger stroke may not deplete the volume of liquid in the syringe.

Pharmaceutical agents housed in syringe 212 can include any compound having a therapeutic effect in a mammal that is experiencing a symptom of a drug or substance overdose. In some embodiments, the drug overdose is from an illegal or recreational drug. In some embodiments, the substance overdose is from an illegal or recreational substance such as, but not limited to, alcohol, smoke, or the like.

Mammals can include humans, equines, canines, felines, bovines, and the like. In one embodiment, an mammal can be a human.

Non-limiting pharmaceutical agents can include a narcotic blocker, an opioid blocker, or a combination thereof. In some embodiments, salts, prodrugs, derivatives and/or analogues of the herein described pharmaceutical agents can be provided alone or in combination.

In some embodiments, pharmaceutical agent(s) included in the herein described syringes can be used to treat a symptom of a drug or substance overdose or the overdose itself. The pharmaceutical agent(s) included in the herein described syringes can be used to treat symptoms such as difficulty breathing, shortness of breath, breathlessness, tightness of throat, slow heartbeat, no heartbeat, weak pulse, dizziness, passing out, blackout, unconsciousness, itching, swelling, itching in the throat, swelling in the throat, vomiting, diarrhea, cramps, or combinations thereof. In some embodiments, the pharmaceutical agent(s) included in the herein described syringes can be used to treat combinations of the above symptoms in an overdose. In still other embodiments, the pharmaceutical agent(s) included in the herein described syringes can be used to treat other symptoms and/or conditions in an emergency situation.

In one embodiment, the pharmaceutical agent is naloxone, salts thereof, derivatives thereof, and/or prodrugs thereof. In one embodiment, naloxone is provided as a HCL dihydrate.

Naloxone, salts thereof, derivatives thereof, and/or prodrugs thereof can be present at a concentration of about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 22 mg/mL, about 24 mg/mL, about 26 mg/mL, about 28 mg/mL, about 30 mg/mL, about 40 mg/mL, about 50 mg/mL, about 60 mg/mL, about 70 mg/mL, about 80 mg/mL, about 90 mg/mL, about 100 mg/mL, between about 5 mg/mL and about 15 mg/mL, between about 10 mg/mL and about 20 mg/mL, between about 10 mg/mL and about 100 mg/mL, between about 1 mg/mL and about 100 mg/mL, between about 50 mg/mL and about 100 mg/mL, at least about 4 mg/mL, at least about 8 mg/mL, at least about 15 mg/mL, at least about 25 mg/mL, or at least about 50 mg/mL. In other embodiments, naloxone, salts thereof, derivatives thereof, and/or prodrugs thereof can be included in syringes described herein to deliver about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 30 mg, about 40 mg, about 50 mg, about 60 mg, about 70 mg, about 80 mg, about 90 mg, about 100 mg, between about 1 mg and about 20 mg, between about 5 mg and about 15 mg, between about 1 mg and about 100 mg, between about 1 mg and about 50 mg, between about 10 mg and about 100 mg, between about 50 mg and about 100 mg, between about 25 mg and about 50 mg, at least about 1 mg, at least about 5 mg, at least about 10 mg, at least about 15 mg, at least about 20 mg, or at least about 50 mg of naloxone in a single injectable dose even if more than that amount is present in the syringe prior to assembly of a syringe device.

In some embodiments, the concentration or dose of naloxone can be administered using a single syringe devices. In other embodiments, the concentration or dose of naloxone can be administered using two or more syringe devices.

In one embodiment, a drug as described herein, salts thereof, derivatives thereof, and/or prodrugs thereof can be in a formulation with a carrier. The formulation can include the drug(s), a salt thereof, derivatives thereof, or prodrugs thereof, one or more tonicity adjuster(s) such as e.g. sodium chloride or other salts, an acid or base to adjust pH, such as e.g. hydrochloric acid or sodium hydroxide, and a solvent or carrier. In some embodiments, the formulation can be in an aqueous formulation and can also include an antioxidant. The antioxidant can be Na-metabisulfite or any other appropriate antioxidant. In still other embodiments, formulations can include an excipient(s) such as but not limited to, a preservative(s), a sorbent(s), a lubricant(s), a vehicle, or the like.

In one embodiment, naloxone, salts thereof, derivatives thereof, and/or prodrugs thereof can be in a formulation with a carrier. The formulation can include naloxone, a salt thereof, derivatives thereof, or prodrugs thereof, one or more tonicity adjuster(s) such as e.g. sodium chloride or other salts, an acid or base to adjust pH, such as e.g. hydrochloric acid or sodium hydroxide, and a solvent or carrier.

In some embodiments, the formulation can be in an aqueous formulation and can also include an antioxidant. The antioxidant can be Na-metabisulfite or any other appropriate antioxidant. In still other embodiments, formulations can include an excipient(s) such as but not limited to, a preservative(s), a sorbent(s), a lubricant(s), a vehicle, or the like.

In some embodiments, the carrier is aqueous. In one embodiment, the carrier is water for injection.

The salt included in a formulation can be any salt. In one embodiment, the salt is sodium chloride, potassium chloride, calcium chloride, ammonium chloride, glycyrrhizic acid, mesitylene sulfonate sodium, chondroitin sulfate, potassium sulfate, monensin sodium salt, sodium hyaluronate, glutamic acid sodium salt, sodium benzoate, magnesium sulfate, or a combination thereof.

In some embodiments, a salt can be included in a formulation to provide an appropriate tonicity.

The acid used to adjust the pH of the formulation can be any acid. In one embodiment, the acid is hydrochloric acid.

In one embodiment, every 1 mL of a formulation can include 5 mg of naloxone.

In one embodiment, every 0.5 mL of a formulation can include 5 mg of naloxone.

In another embodiment, every 1 mL of a formulation can include 15 mg of naloxone.

In another embodiment, every 0.5 mL of a formulation can include 15 mg of naloxone.

In one embodiment, a drug formulation is provided that includes naloxone, sodium chloride, water for injection, and hydrochloric acid as needed to adjust pH. In another embodiment, a drug formulation is provided that includes 2.2 g of naloxone, 1.67 g of sodium chloride, 200 g of water for injection, and 1% hydrochloric acid as needed to adjust pH. In some embodiments, 1 g of naloxone HCl is equivalent to 1.11 g of naloxone HCL dihydrate and is adjusted for purity.

In some embodiments, the drugs can be filled into the syringes in a particular or specific amount. That particular amount can be about 0.2 cc, about 0.3 cc, about 0.4 cc, about 0.5 cc, about 0.6 cc, about 0.7 cc, about 0.8 cc, about 0.9 cc, about 1 cc, about 2 cc, between about 0.4 cc and about 0.6 cc, between about 0.1 cc and about 1 cc, between about 0.3 cc and about 0.7 cc. In one embodiment, the filling volume can be about 0.5 cc.

Figure 4:
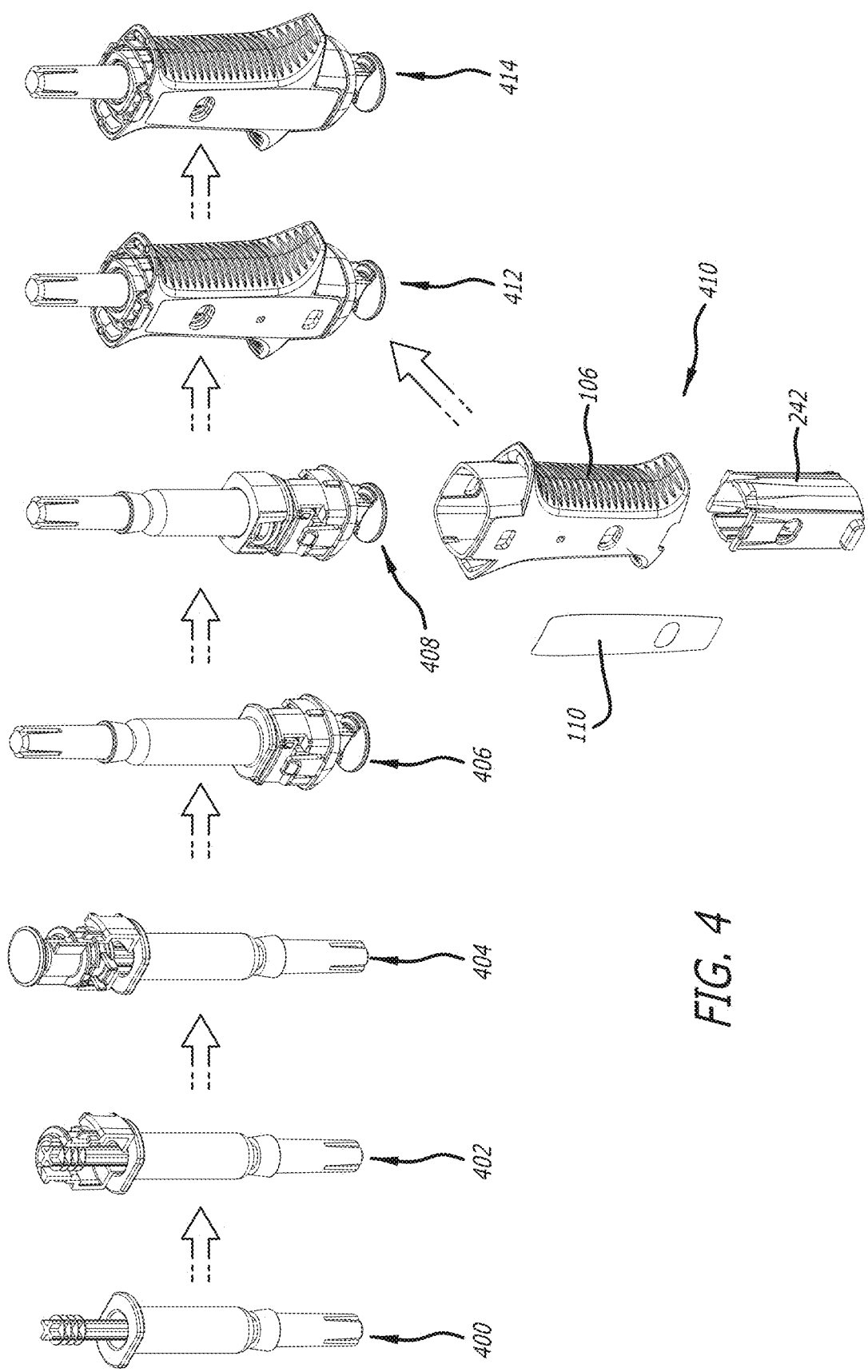
FIG. 4 illustrates a non-limiting assembly method for the syringe devices as described herein.

FIG. 4 illustrates a non-limiting assembly method for the syringe devices as described herein. As a first step 400, a syringe is filled with a desired drug, and if desired, an appropriately sized gas bubble. In some embodiments, a bubble is not included and/or is not needed. A plunger rod is then screwed to the syringe's stopper. In a second step 402, a spacer is added around the plunger rod. In a next step 404, the actuator is attached opposite the spacer. A top is then placed on the spacer and actuator to complete the plunger assembly in a fourth step 406. A spring and a syringe stop ring are then slid down around the syringe body until they meet the syringe's flange in a fifth step 408.

Separately, in step 410 a needle guard is added to an empty encasement and retracted into the encasement. Appropriate label(s) are added to the encasement in step 410 as well.

Next, in step 412, the encasement is then slid over the syringe that includes the plunger assembly and snapped into place attached to the top's teeth. Any additional labels can be added to complete the assembly of the herein described syringe in step 414.

In some embodiments, the syringe devices are single use and/or disposable. Such single use devices are generally used for a single treatment and then discarded in an appropriate manner consistent with health regulations.

In some embodiments, the contents of syringe devices and devices themselves are sterile. Sterile syringe devices can be obtained by sterile filling and device assembly or by sterilizing the syringe devices after assembly. The syringe devices described herein can be sterilized using conventional sterilization techniques such as, but not limited to gamma irradiation techniques.

Syringe devices described herein can be packaged for distribution to users. Packaging can take on forms that can at least partially encase or cover portions of the syringe devices that may be conducive to interference. In one embodiment, syringe devices can be fully encased.

An example case for syringe device 100 is illustrated in FIGS. 5A-C, 6, and 7. Case 500 can be opened and closed on a hinge 502 and a locking mechanism 504. Locking mechanism 504 can allow for a single use or multiple uses. In one embodiment, locking mechanism 504 can be a hook and catch mechanism.

Case 500 can be shaped to fit a single syringe device. FIG. 5C illustrates a syringe device 100 loaded in case 500. In one embodiment, case 500 can be configured to be at least as long as syringe device 100 from the tip of a needle cover to the top of an actuator finger surface in a ready to use configuration. In other embodiments, case 500 can be configured to hold syringe device 100 in an angled configuration.

Figure 7:
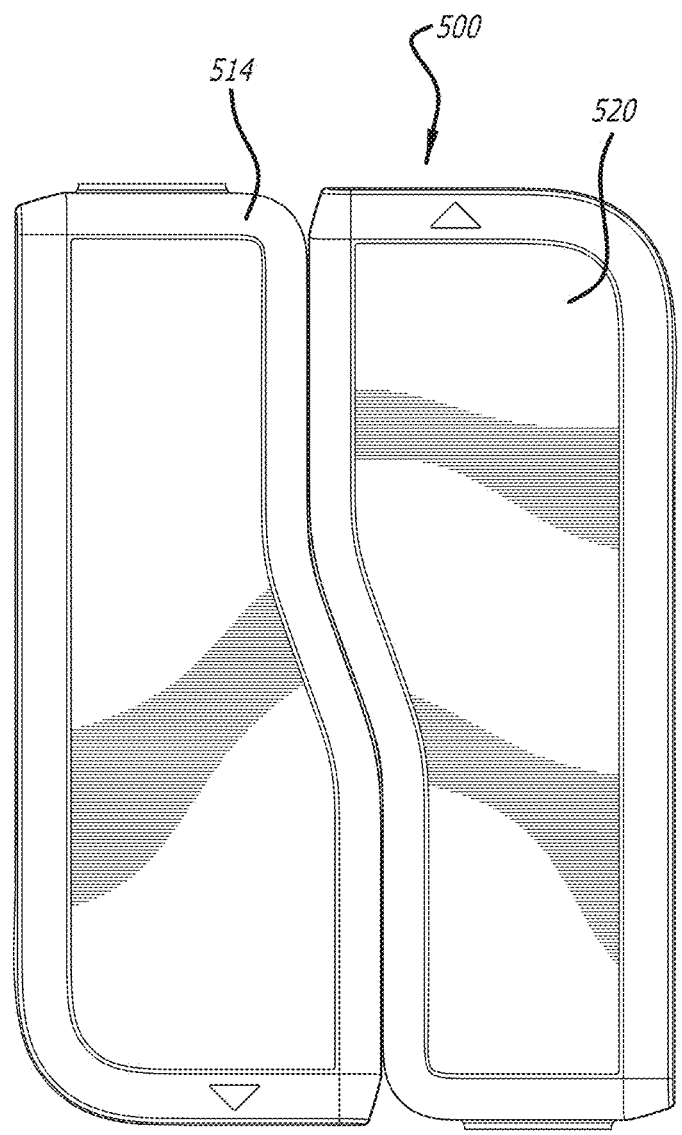
FIG. 7 illustrates two cases coupled together to form a single unit.

Allowing syringe device 100 to sit at angle 506 can allow for case 500 to have a wider bottom portion 508 than top portion 510. Because top portion 510 and bottom portion 508 are not the same, a non-linear edge 512 is created. A second case 514 as illustrated in FIG. 7 can be spun 180 degrees and the non-linear edge of each can be matched up.

Figures 5A, 5B:
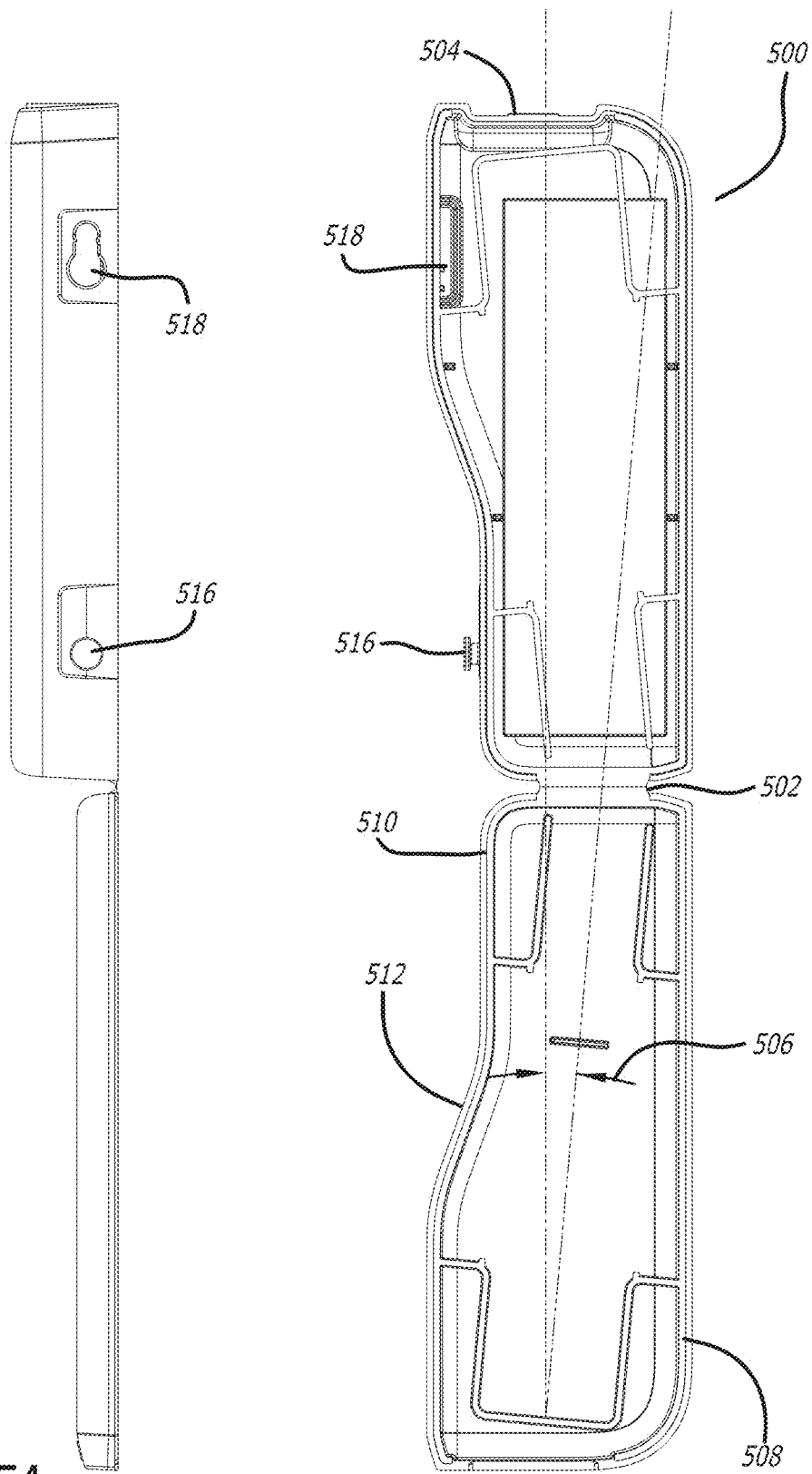
FIG. 5A illustrates a side view of a case for the syringe devices described herein in an open configuration.
FIG. 5B illustrates a top view of a case for the syringe devices described herein in an open configuration without a syringe device.
Figure 6:
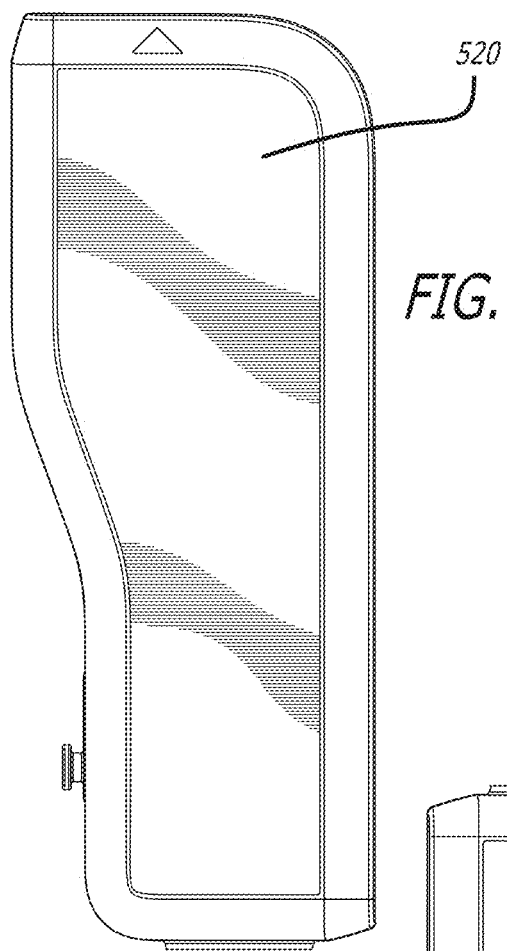
FIG. 6 illustrates a case of FIGS. 5A-C in a closed configuration.

Angle 506 shown in FIG. 5B can be about 3 degrees, about 4 degrees, about 5 degrees, about 6 degrees, about 7 degrees, about 8 degrees, about 9 degrees, about 10 degrees, between about 3 degrees and about 8 degrees, between about 4 degrees and about 6 degrees, or at least about 3 degrees. In one embodiment, angle 506 is about 5 degrees.

In some embodiments, each case can include a fastening nub 516 and a receiving orifice 518 can be included on non-linear edge 512. Receiving orifice 518 can have a key hole configuration allowing for fastening nub 516 to be inserted into the larger portion of the key hole and slid and locked into place. Thus, when case 500 and second case 514 are mated, two sets of fastening nubs and receiving orifices can be used to hold the two cases together.

Fitting two cases together can allow a user to carry a single dose of a drug in case of an emergency and have a second dose close at hand in case a second dosage is needed. FIG. 7 illustrates two cases joined together. Angling the syringe device within a case allows for the overall length of the case to be reduced. The extra width of a case is mitigated by the ability to join two cases together with an overall joined width that is less than double the width of a single case. Thus, this joined configuration can meet a need to have multiple dosages with a small physical footprint.

Case 500 (or second case 514) can include one or more labels that provide information about the drug or drugs being delivered via an enclosed syringe device. As illustrated in FIGS. 5A-C, 6, and 7, case label 520 can cover substantially an entire surface of case 500. However, in other embodiments, case label 520 may cover less than an entire surface of case 500 or multiple labels can be used instead of one large label. In fact, in some embodiments, any number of labels of any shapes can be used to label a case as needed.

Cases can be formed of any appropriate material that can house the described syringes through loading, shipping, regular carrying by patients, and the like without damage to an enclosed syringe device. In some embodiments, cases can be formed of a polymeric material such as a thermoplastic. In one embodiment, cases can be formed of a polypropylene material. Cases can be extruded, blow molded, or the like.

Cases can be textured on portions of their surface in order to allow a user to easily grip a case(s). In one embodiment, cases can be textured using MT-11010.

Cases can have identification markers such as an arrow(s) indicating which side of the case is used to open it. In some embodiments, raised features can be used so that a user when administering an injection to a patient in an emergency drug overdose can open the case without actually focusing on it. Also, in some embodiments, by including a non-linear edge, tactile opening of the case can be accomplished knowing that the thicker end of the case is opened.

Further, cases can be color coded to indicate a particular drug. Cases can be color coded to indicate the order of use of the enclosed syringe device.

Figure 8:
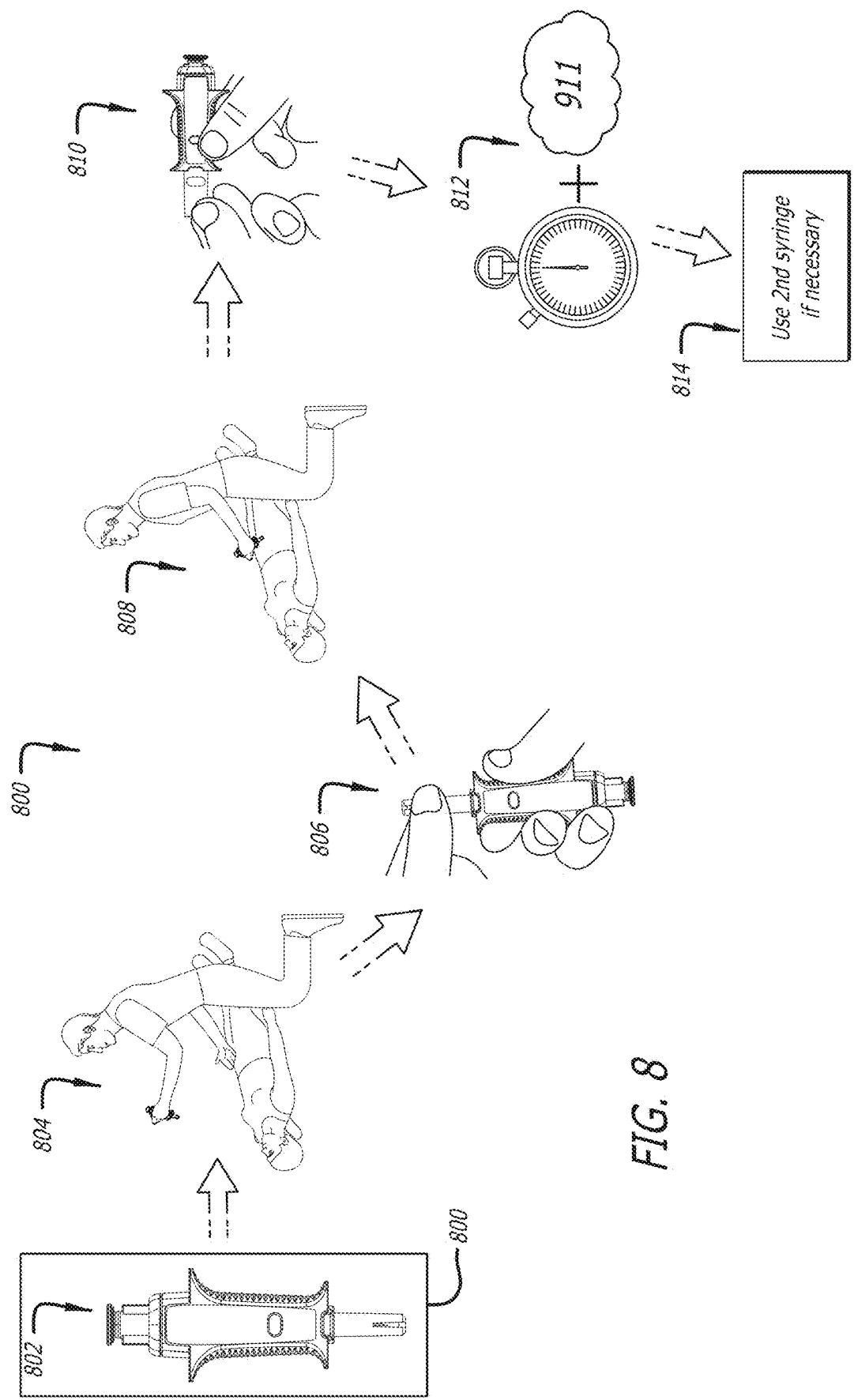
FIG. 8 illustrates a non-limiting method of using the herein described syringe devices.

An example use of a syringe device as described herein is illustrated in FIG. 8. FIG. 8 is illustrated in the context of the non-limiting use of naloxone and illustrates an instruction insert 800. Insert 800 includes a diagram 802 of the syringe device itself, labeling the various use parts of the device for a clear illustration for a user during an emergency drug overdose situation (parts not labeled for simplicity).

As a first step 804, the user is instructed to remove a syringe device from a container and examine the patient for an appropriate injection site. In one embodiment, the injection can be on the thigh. Although described as using a thigh, other injection sites can be used, such as but not limited to the arm, stomach, buttocks, abdomen, and the like. In some embodiments, injections can be made into muscles.

As a second step 806, a user is instructed to remove the needle cap with the syringe device pointing up.

As a third step 808, a user is shown how to properly hold the syringe device for injection. The user is instructed to inject the patient and put the needle in until it is no longer visible. The plunger (actuator) is pushed until it stops and clicks. The audible click is an indication to the user that the drug has been fully injected. The user is instructed to leave the needle in the skin for an additional two seconds to allow proper absorption. Further, the user is told that excess liquid will remain in the syringe device.

The user is instructed in a forth step 810 to remove the needle and slide the needle guard over the needle. The user then places that syringe device back in the case and snaps the case closed.

Optionally, the user is instructed to massage the location for about 10 seconds. In other embodiments, longer or shorter massages may be required, such as but not limited to, about 5 seconds, about 15 seconds, about 20 seconds, about 25 seconds, about 30 seconds, between about 5 seconds and about 20 seconds, between about 10 seconds and about 20 seconds, at least about 5 seconds, or at least about 10 seconds.

As a fifth step 812 the user is instructed to wait a given time period to determine if the injection has been effective. This time period can be at least about 10 seconds, at least about 20 seconds, at least about 30 seconds, at least about 1 minute, or at least about 5 minutes. Effectiveness can manifest in events including a sensed heartbeat, a stronger heartbeat, breathing, movement, or the like.

The user is instructed to seek medical help and/or to call an emergency line (e.g., 911). The user is told to inform the medical help that they just administered an injection of naloxone. The user is further instructed to give the used needle case including the used syringe device to the medical workers when they arrive.

If the injection is ineffective, the user is told to use the second syringe device if needed as a sixth step 814.

The user is instructed that seeking medical help and/or to calling an emergency line (e.g., 911) can occur at any time during the process. The user need not wait until step five to seek emergency medical help.

In some embodiments, the syringe devices described herein can be provided as systems or kits. These systems and kits can include a syringe device enclosed in a container with instructions for use.

In other embodiments, systems and kits can include two syringe devices each enclosed in a separate container each with instructions for use. In still other embodiments, a system or kit can include two syringe device filled containers that are connected as described herein.

In one embodiment, systems and kits can include a syringe device filled with a therapeutic amount of a drug enclosed in a container with instructions for use. In other embodiments, systems and kits can include two syringe devices each filled with a therapeutic amount of a drug, each enclosed in a separate container, and each including instructions for use. In still other embodiments, a system or kit can include two syringe devices filled with a therapeutic amount of a drug in containers that are connected as described herein.

In one embodiment, systems and kits can include a syringe device filled with a therapeutic amount of an opioid antagonist enclosed in a container with instructions for use. In other embodiments, systems and kits can include two syringe devices each filled with a therapeutic amount of opioid antagonist, each enclosed in a separate container, and each including instructions for use. In still other embodiments, a system or kit can include two syringe devices filled with a therapeutic amount of opioid antagonist in containers that are connected as described herein.

In one embodiment, systems and kits can include a syringe device filled with a therapeutic amount of naloxone enclosed in a container with instructions for use. In other embodiments, systems and kits can include two syringe devices each filled with a therapeutic amount of naloxone, each enclosed in a separate container, and each including instructions for use. In still other embodiments, a system or kit can include two syringe devices filled with a therapeutic amount of naloxone in containers that are connected as described herein.

In some embodiments, a syringe device(s) can be distributed to a patient without a drug included within it. The syringe device(s) can be loaded into cases. These syringe devices can be used as training devices to allow a potential user to understand how the syringe device works so that in an emergency overdose situation, they will be ready to use an actual syringe device. In some embodiments, a training device may not include a needle so that a trainee can partake in all the steps except the needle injection portion.

In some embodiments, the syringe devices described herein can prevent a user from unscrewing the plunger rod from the stopper. This prevention ability of the presently described syringe devices can disallow a change in travel stroke and hence delivered drug volume of traditional syringes. Further, the syringe devices described herein can prevent a user moving the plunger rod and/or stopper thereby affecting the delivery volume of a drug filled syringe device. Further still, the presently described syringe devices can prevent a user from pulling out and/or back the stopper/plunger rod thereby altering the delivered volume and the purity of the drug.

As discussed, the presently described syringe devices can provide tactical feedback to alert a user of a complete drug dose delivery. Typical syringes only allow a tactical feedback when the stopper and/or plunger reach an end stop.

The presently described syringe devices can also prevent a user from modifying the plunger and/or stopper to alter the amount of preset drug delivery. The present syringe devices can deliver a preset drug dosage without intervention by the user that can alter an amount of drug delivered.

The presently described syringe devices can prevent suboptimal drug injections by preventing unexpected syringe delivery orientations. Syringes can generally provide optimal delivery of drugs when oriented in a particular angle for injection. The present syringe devices can provide a surface that can press against the injection site and effectively hold the syringe devices at a predetermined angle for injection.

In some embodiments, the presently described syringe devices do not include electronics. In some embodiments, the presently described syringe devices do not include a battery or batteries. In some embodiments, the presently described syringe devices do not include a circuit board. In some embodiments, the presently described syringe devices do not include an energy source to move the actuator.

Also provided herein are compositions and methods for treating opioid overdose. In some embodiments, the opioid overdose can be from fentanyl or an analogue or derivative thereof. The compositions can include a high dose of naloxone. In some embodiments, administration of the compositions can be by the syringe devices as described herein.

In some embodiments, the compositions can be used to treat fentanyl overdose. In some embodiments, the compositions can be used to prevent fentanyl overdose deaths.

The compositions described can be delivered administered to a mammal using standard administration techniques, including oral, intravenous, intraperitoneal, subcutaneous, pulmonary, transdermal, intramuscular, inhalation, intranasal, buccal, vaginal, sublingual, suppository administration, or a combination thereof. In some embodiments, administration is by injection. In one embodiment, the injection can be intramuscular. In other embodiments, administration is by inhalation. In some embodiments, administration is by syringe devices as described herein.

Mammals can include, but are not limited to, humans, horses, camels, dogs, cats, cows, bears, rodents, oxen, bison, buffalo, caribou, moose, deer, elk, sheep, goats, pigs, rabbits, pouched mammals, primates, carnivores, and the like. In one embodiment, the mammal is a human.

In some embodiments, the compositions can be used to treat a symptom of a drug or substance overdose or the overdose itself. The compositions can be used to treat symptoms such as difficulty breathing, shortness of breath, breathlessness, tightness of throat, slow heartbeat, no heartbeat, weak pulse, dizziness, passing out, blackout, unconsciousness, itching, swelling, itching in the throat, swelling in the throat, vomiting, diarrhea, cramps, or combinations thereof. In some embodiments, the compositions can be used to treat combinations of the above symptoms in an overdose. In still other embodiments, the compositions can be used to treat other symptoms and/or conditions in an emergency situation.

In one embodiment, the naloxone can include salts, derivatives thereof, and/or prodrugs thereof. In one embodiment, naloxone is provided as a HCL dihydrate.

Naloxone, salts thereof, derivatives thereof, and/or prodrugs thereof can be present at a high dose, such as greater than about 4 mg. In some embodiments, the dose can be greater than about 5 mg, greater than about 6 mg, greater than about 7 mg, greater than about 8 mg, greater than about 9 mg, greater than about 10 mg, greater than about 20 mg, greater than about 30 mg, greater than about 40 mg, greater than about 50 mg, greater than about 100 mg, greater than about 200 mg, greater than about 250 mg, greater than about 300 mg, greater than about 400 mg, or greater than about 500 mg. In some embodiments, the dose is about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 400 mg, about 500 mg, between about 5 mg and about 20 mg, between about 5 mg and about 15 mg, between about 5 mg and about 100 mg, between about 5 mg and about 50 mg, between about 10 mg and about 100 mg, between about 50 mg and about 100 mg, between about 25 mg and about 50 mg, between about 5 mg and about 500 mg, between about 5 mg and about 300 mg, between about 5 mg and about 400 mg, or between about 5 mg and about 250 mg of naloxone.

In one embodiment, naloxone can be in a formulation with a carrier. The formulation can include naloxone, one or more tonicity adjuster(s) such as e.g. sodium chloride or other salts, an acid or base to adjust pH, such as e.g. hydrochloric acid or sodium hydroxide, and a solvent or carrier. In some embodiments, the formulation can be in an aqueous formulation and can also include an antioxidant. The antioxidant can be Na-metabisulfite or any other appropriate antioxidant. In still other embodiments, formulations can include an excipient(s) such as but not limited to, a preservative(s), a sorbent(s), a lubricant(s), a vehicle, or the like.

In one embodiment, a high dose naloxone composition can include one or more tonicity adjuster(s) such as e.g. sodium chloride or other salts, an acid or base to adjust pH, such as e.g. hydrochloric acid or sodium hydroxide, and a solvent or carrier.

In some embodiments, the composition can be aqueous and can also include an antioxidant. The antioxidant can be Na-metabisulfite or any other appropriate antioxidant. In still other embodiments, compositions can include an excipient(s) such as but not limited to, a preservative(s), a sorbent(s), a lubricant(s), a vehicle, or the like.

In some embodiments, the carrier is aqueous. In one embodiment, the carrier is water for injection.

The salt included in a formulation can be any salt. In one embodiment, the salt is sodium chloride, potassium chloride, calcium chloride, ammonium chloride, glycyrrhizic acid, mesitylene sulfonate sodium, chondroitin sulfate, potassium sulfate, monensin sodium salt, sodium hyaluronate, glutamic acid sodium salt, sodium benzoate, magnesium sulfate, or a combination thereof.

In some embodiments, a salt can be included in a formulation to provide an appropriate tonicity.

The acid used to adjust the pH of the formulation can be any acid. In one embodiment, the acid is hydrochloric acid.

In one embodiment, a drug formulation is provided that includes naloxone, sodium chloride, water for injection, and hydrochloric acid as needed to adjust pH.

In some embodiments, a dose of 1 mg/0.5 mL, 2 mg/0.5 mL, 3 mg/0.5 mL, 4 mg/0.5 mL, 5 mg/0.5 mL, 6 mg/0.5 mL, 7 mg/0.5 mL, 8 mg/0.5 mL, 9 mg/0.5 mL, 10 mg/0.5 mL, 15 mg/0.5 mL, 20 mg/0.5 mL, 25 mg/0.5 mL, 30 mg/0.5 mL, about 1 mg/0.5 mL, about 2 mg/0.5 mL, about 3 mg/0.5 mL, about 4 mg/0.5 mL, about 5 mg/0.5 mL, about 6 mg/0.5 mL, about 7 mg/0.5 mL, about 8 mg/0.5 mL, about 9 mg/0.5 mL, about 10 mg/0.5 mL, about 15 mg/0.5 mL, about 20 mg/0.5 mL, about 25 mg/0.5 mL, about 30 mg/0.5 mL, at least 1 mg/0.5 mL, at least 2 mg/0.5 mL, at least 3 mg/0.5 mL, at least 4 mg/0.5 mL, at least 5 mg/0.5 mL, at least 6 mg/0.5 mL, at least 7 mg/0.5 mL, at least 8 mg/0.5 mL, at least 9 mg/0.5 mL, at least 10 mg/0.5 mL, at least 15 mg/0.5 mL, at least 20 mg/0.5 mL, at least 25 mg/0.5 mL, at least 30 mg/0.5 mL, at most 1 mg/0.5 mL, at most 2 mg/0.5 mL, at most 3 mg/0.5 mL, at most 4 mg/0.5 mL, at most 5 mg/0.5 mL, at most 6 mg/0.5 mL, at most 7 mg/0.5 mL, at most 8 mg/0.5 mL, at most 9 mg/0.5 mL, at most 10 mg/0.5 mL, at most 15 mg/0.5 mL, at most 20 mg/0.5 mL, at most 25 mg/0.5 mL, at most 30 mg/0.5 mL, between about 1 mg/0.5 mL to about 5 mg/0.5 mL, between about 1 mg/0.5 mL to about 10 mg/0.5 mL, between about 5 mg/0.5 mL to about 15 mg/0.5 mL, between about 10 mg/0.5 mL to about 20 mg/0.5 mL, between about 15 mg/0.5 mL to about 25 mg/0.5 mL, or between about 20 mg/0.5 mL to about 30 mg/0.5 mL intramuscular naloxone hydrochloride can be administered. This formulation can be administered via a pre-filled syringe or auto injector. In some embodiments, this formulation can be administered by syringe devices as described herein.

In other embodiments, a dose of 1 mg/0.4 mL, 2 mg/0.4 mL, 3 mg/0.4 mL, 4 mg/0.4 mL, 5 mg/0.4 mL, 6 mg/0.4 mL, 7 mg/0.4 mL, 8 mg/0.4 mL, 9 mg/0.4 mL, 10 mg/0.4 mL, 15 mg/0.4 mL, 20 mg/0.4 mL, 25 mg/0.4 mL, 30 mg/0.4 mL, about 1 mg/0.4 mL, about 2 mg/0.4 mL, about 3 mg/0.4 mL, about 4 mg/0.4 mL, about 5 mg/0.4 mL, about 6 mg/0.4 mL, about 7 mg/0.4 mL, about 8 mg/0.4 mL, about 9 mg/0.4 mL, about 10 mg/0.4 mL, about 15 mg/0.4 mL, about 20 mg/0.4 mL, about 25 mg/0.4 mL, about 30 mg/0.4 mL, at least 1 mg/0.4 mL, at least 2 mg/0.4 mL, at least 3 mg/0.4 mL, at least 4 mg/0.4 mL, at least 5 mg/0.4 mL, at least 6 mg/0.4 mL, at least 7 mg/0.4 mL, at least 8 mg/0.4 mL, at least 9 mg/0.4 mL, at least 10 mg/0.4 mL, at least 15 mg/0.4 mL, at least 20 mg/0.4 mL, at least 25 mg/0.4 mL, at least 30 mg/0.4 mL, at most 1 mg/0.4 mL, at most 2 mg/0.4 mL, at most 3 mg/0.4 mL, at most 4 mg/0.4 mL, at most 5 mg/0.4 mL, at most 6 mg/0.4 mL, at most 7 mg/0.4 mL, at most 8 mg/0.4 mL, at most 9 mg/0.4 mL, at most 10 mg/0.4 mL, at most 15 mg/0.4 mL, at most 20 mg/0.4 mL, at most 25 mg/0.4 mL, at most 30 mg/0.4 mL, between about 1 mg/0.4 mL to about 5 mg/0.4 mL, between about 1 mg/0.4 mL to about 10 mg/0.4 mL, between about 5 mg/0.4 mL to about 15 mg/0.4 mL, between about 10 mg/0.4 mL to about 20 mg/0.4 mL, between about 15 mg/0.4 mL to about 25 mg/0.4 mL, or between about 20 mg/0.4 mL to about 30 mg/0.4 mL intramuscular naloxone hydrochloride can be administered. This formulation can be administered via a pre-filled syringe or auto injector. In some embodiments, this formulation can be administered by syringe devices as described herein.

In other embodiments, a dose of 1 mg/2 mL, 2 mg/2 mL, 3 mg/2 mL, 4 mg/2 mL, 5 mg/2 mL, 6 mg/2 mL, 7 mg/2 mL, 8 mg/2 mL, 9 mg/2 mL, 10 mg/2 mL, 15 mg/2 mL, 20 mg/2 mL, 25 mg/2 mL, 30 mg/2 mL, about 1 mg/2 mL, about 2 mg/2 mL, about 3 mg/2 mL, about 4 mg/2 mL, about 5 mg/2 mL, about 6 mg/2 mL, about 7 mg/2 mL, about 8 mg/2 mL, about 9 mg/2 mL, about 10 mg/2 mL, about 15 mg/2 mL, about 20 mg/2 mL, about 25 mg/2 mL, about 30 mg/2 mL, at least 1 mg/2 mL, at least 2 mg/2 mL, at least 3 mg/2 mL, at least 4 mg/2 mL, at least 5 mg/2 mL, at least 6 mg/2 mL, at least 7 mg/2 mL, at least 8 mg/2 mL, at least 9 mg/2 mL, at least 10 mg/2 mL, at least 15 mg/2 mL, at least 20 mg/2 mL, at least 25 mg/2 mL, at least 30 mg/2 mL, at most 1 mg/2 mL, at most 2 mg/2 mL, at most 3 mg/2 mL, at most 4 mg/2 mL, at most 5 mg/2 mL, at most 6 mg/2 mL, at most 7 mg/2 mL, at most 8 mg/2 mL, at most 9 mg/2 mL, at most 10 mg/2 mL, at most 15 mg/2 mL, at most 20 mg/2 mL, at most 25 mg/2 mL, at most 30 mg/2 mL, between about 1 mg/2 mL to about 5 mg/2 mL, between about 1 mg/2 mL to about 10 mg/2 mL, between about 5 mg/2 mL to about 15 mg/2 mL, between about 10 mg/2 mL to about 20 mg/2 mL, between about 15 mg/2 mL to about 25 mg/2 mL, or between about 20 mg/2 mL to about 30 mg/2 mL intramuscular naloxone hydrochloride can be administered. This formulation can be administered via a pre-filled syringe or auto injector. In some embodiments, this formulation can be administered by syringe devices as described herein.

In other embodiments, a dose greater than or equal to about 5 mg of intramuscular naloxone can be administered. The dose can include naloxone hydrochloride at a dose of 5 mg/0.5 mL.

In some embodiments, administering a high dose naloxone composition, as described herein, can result in a maximum observed plasma concentration ($C_{max}$) of 15.8 ng/mL. In other embodiments, $C_{max}$ can be 17.2 ng/mL. In some embodiments, the $C_{max}$ can be 3.58 ng/mL. In some embodiments, the Cmax is about 3 ng/mL, about 3.24 ng/mL, about 3.58 ng/mL, about 4 ng/mL, about 5 ng/mL, about 6 ng/mL, about 7 ng/mL, about 8 ng/mL, about 9 ng/mL, about 10 ng/mL, about 11 ng/mL, about 12 ng/mL, about 13 ng/mL, about 14 ng/mL, about 15 ng/mL, about 15.8 ng/mL, about 16 ng/mL, about 17 ng/mL, about 17.2 ng/mL, about 18 ng/mL, about 19 ng/mL, about 20 ng/mL, about 21 ng/mL, about 22 mg/mL, about 23 ng/mL, about 24 ng/mL, between about 1 ng/mL to about 20 ng/mL, between about 3 ng/mL to about 16 ng/mL, between about 3 ng/mL to about 17.5 ng/mL, between about 5 ng/mL to about 20 ng/mL, between about 10 ng/mL to about 20 ng/mL, between about 1 ng/mL to about 24 ng/mL, between about 15 ng/mL to about 24 ng/mL, or between about 10 ng/mL to about 24 ng/mL.

In other embodiments, administering a high dose naloxone composition, as described herein, can result in an area under the plasma concentration-time curve from 0 to the time of the last measureable plasma concentration ($AUC_{0-1}$) can be 0.0129 h*ng/mL at an AUC from time 0 to 2.5 minutes ($AUC_{0-0.04h}$). In some embodiments, the $AUC_{0-0.04h}$ can be about 0.001 h*ng/mL, about 0.002 h*ng/mL, about 0.003 h*ng/mL, about 0.004 h*ng/mL, about 0.00496 h*ng/mL, about 0.005 h*ng/mL, about 0.006 h*ng/mL, about 0.007 h*ng/mL, about 0.008 h*ng/mL, about 0.009 h*ng/mL, about 0.01 h*ng/mL, about 0.011 h*ng/mL, about 0.012 h*ng/mL, about 0.0129 h*ng/mL, about 0.013 h*ng/mL, about 0.014 h*ng/mL, about 0.015 h*ng/mL, about 0.02 h*ng/mL, about 0.03 h*ng/mL, about 0.04 h*ng/mL, about 0.05 h*ng/mL, about 0.06 h*ng/mL, about 0.07 h*ng/mL, about 0.08 h*ng/mL, about 0.09 h*ng/mL, about 0.1 h*ng/mL, about 0.2 h*ng/mL, about 0.3 h*ng/mL, about 0.4 h*ng/mL, about 0.5 h*ng/mL, about 0.6 h*ng/mL, about 0.7 h*ng/mL, about 0.8 h*ng/mL, about 0.9 h*ng/mL, about 1 h*ng/mL, more than 0.012 h*ng/mL, less than 0.013 h*ng/mL, between about 0.005 h*ng/mL to about 0.013 h*ng/mL, or between about 0.012 h*ng/mL to about 0.013 h*ng/mL, between about 0.001 h*ng/mL to about 0.01 h*ng/mL, between about 0.01 h*ng/mL to about 0.1 h*ng/mL, between about 0.01 h*ng/mL to about 0.02 h*ng/mL, or between about 0.012 h*ng/mL to about 0.0129 h*ng/mL In some embodiments, administering a high dose naloxone composition, as described herein, can result in an area under the plasma concentration-time curve from 0 to the time of the last measureable plasma concentration ($AUC_{0-1}$) can be 0.0782 h*ng/mL at an AUC from time 0 to 5 minutes ($AUC_{0-0.08h}$). In some embodiments, the $AUC_{0-0.08h}$ can be about 0.001 h*ng/mL, about 0.002 h*ng/mL, about 0.003 h*ng/mL, about 0.004 h*ng/mL, about 0.005 h*ng/mL, about 0.006 h*ng/mL, about 0.007 h*ng/mL, about 0.008 h*ng/mL, about 0.009 h*ng/mL, about 0.01 h*ng/mL, about 0.011 h*ng/mL, about 0.012 h*ng/mL, about 0.013 h*ng/mL, about 0.014 h*ng/mL, about 0.015 h*ng/mL, about 0.016 h*ng/mL, about 0.017 h*ng/mL, about 0.018 h*ng/mL, about 0.019 h*ng/mL, about 0.0192 h*ng/mL about 0.02 h*ng/mL, about 0.03 h*ng/mL, about 0.04 h*ng/mL, about 0.05 h*ng/mL, about 0.06 h*ng/mL, about 0.07 h*ng/mL, about 0.0782 h*ng/mL, about 0.08 h*ng/mL, about 0.09 h*ng/mL, about 0.1 h*ng/mL, about 0.2 h*ng/mL, about 0.3 h*ng/mL, about 0.4 h*ng/mL, about 0.5 h*ng/mL, about 0.6 h*ng/mL, about 0.7 h*ng/mL, about 0.8 h*ng/mL, about 0.9 h*ng/mL, about 1 h*ng/mL, more than 0.078 h*ng/mL, less than 0.079 h*ng/mL, between about 0.078 h*ng/mL to about 0.079 h*ng/mL, or between about 0.019 h*ng/mL to about 0.02 h*ng/mL, between about 0.0191 h*ng/mL to about 0.0791 h*ng/mL, between about 0.05 h*ng/mL to about 0.10 h*ng/mL, between about 0.05 h*ng/mL to about 0.20 h*ng/mL, or between about 0.05 h*ng/mL to about 1 h*ng/mL The herein described naloxone compositions can increase the dose of intramuscular naloxone to better reverse opioid intoxication.

In today's opioid overdose paradigm, without a dose of naloxone as described, eg. high doses, the risk of inadequate reversal of the opioid toxicity far exceeds the risk of over antagonizing the respiratory depression and precipitating opioid withdrawal syndrome. Administering naloxone as described may be a countermeasure that can be initiated rapidly in an attempt to lower the morbidity and mortality.

Opioids can include any type of opioid such as but not limited to codeine, morphine, oxycodone, hydrocodone, tramadol, methadone, carfentanil, lofentanil, hydromorphine, tapentadol, anileridine, levorphanol, buprenorphine, heroine, fentanyl, or a combination thereof.

In additional to fentanyl, more potent analogues such as carfentanil and lofentanil may require even higher doses of naloxone. Naloxone resistance may occur at doses which previously reversed morphine effects. In some embodiments, naloxone compositions can be used to treat carfentanil overdose. In some embodiments, naloxone compositions can be used to treat lofentanil overdose.

Naloxone is an opioid antagonist used for the acute treatment of opioid overdoses. There has been a dramatic increase of deaths due to fentanyl, some requiring multiple doses of naloxone. Fentanyl differs from other opiates as having a very rapid onset and transport out of the central nervous system. Fentanyl is therefore widely distributed in the central nervous system (CNS). Furthermore, a high range of systemic levels of fentanyl have been observed in overdose victims. Thus, in some embodiments, high doses of naloxone may be needed to combat this new era of overdoses. The concern remains that in the current opioid epidemic, without higher doses of naloxone, the risk of inadequate reversal of the opioid toxicity far exceeds the risk of over antagonizing the respiratory depression and precipitating opioid withdrawal syndrome.

On Apr. 5, 2018, the Surgeon General of the U.S. Public Health Service released a health advisory on urging the expansion of the use and access for naloxone, an opioid antagonist, to counter the ongoing opioid epidemic. The Surgeon General's recommendation was a result of a culmination of epidemiological data suggesting a sizable and rapid increase in opioid related deaths in the United States. Opioid related deaths in the United States currently averages 115 deaths/day. New data released from the Centers for Disease Control (CDC) suggests a rise of almost 10% of deaths due to opioid overdoses killing approximately 72,000 Americans, a record number in 2017. This death toll is higher than the peak yearly death totals from HIV, car crashes, or gun deaths.

Indeed, the number of deaths due to opioids has dramatically increased over five-fold compared to 1999. Although the epidemiological data suggests that there may be rises in heroin and semisynthetic opioid use, the Center for Disease Control (CDC) has attributed the largest increase in deaths to illicitly manufactured synthetic opioids, such as fentanyl.

This increase in opioid deaths has been described as the third wave or the synthetic opioid era.

According to the CDC, drug overdose deaths continue to increase in the United States. Opioid related deaths involve both men and women of all races and adults of nearly all age groups. Although opioid abuse has been a significant public health problem in the past, the recent dramatic rise of deaths appears to be related to the abundance of synthetic opioids. This problem requires alternative countermeasures to deal with the significant increase in deaths. The abrupt increase in synthetic opioid deaths was further substantiated by an analysis that separated synthetic opioids, such as fentanyl, into a unique category during the years of 2013-2016. Overall, the analysis revealed an 87.7% increase in deaths associated with synthetic opioids. In contrast, death rates due to natural and semisynthetic opioids remained relatively stable. However, the continuing rise of illicitly manufactured fentanyl has created new challenge for the adequate treatment of overdoses.

In some embodiments, compositions and methods are described herein include naloxone. In some embodiments, compositions and methods are described herein include high doses of naloxone. In some embodiments, compositions and methods are described herein can be useful when taking into account the era of synthetic opioids.

Naloxone is a semi-synthetic N-allyl derivative of oxymorphone that antagonizes opioids. It is a specific opioid antagonist that acts competitively at opioid receptors without agonistic or morphine-like properties characteristic of other narcotic antagonists (eg., nalorphine, levallorphan). Naloxone is used to reverse opioid central depression, including respiratory depression, induced by natural or synthetic opioids, in the management of known or suspected opioid overdose, postoperatively after the use of opioids during surgery, and in neonates when opioid analgesics have been given to the mother during labor.

It can antagonize the three opiate receptors in the brain (p, k, and a). The drug onset is related to its rapid entry into the brain, which is 12 to 15 times greater brain to serum ratio compared to morphine, primarily due to its high lipophilicity. The distribution half-life for naloxone is suggested to be 4.7 minutes while the elimination half-life averages 65 minutes. Naloxone competitively inhibits most opioids rapidly. However, the shorter duration of activity may play a role in the re-narconization of some longer acting opioids which can result in reoccurrence of toxicity and respiratory depression. For example, in a study, 16 healthy volunteers received intravenous morphine at 0.15 mg/kg and were reversed with low dose of naloxone (0.4 mg). Interestingly, there was a return to severe respiratory depression within 30 minutes. However, the issue of re-narconization may not be a major factor for shorter acting opioids such as fentanyl.

The reversal effect(s) of naloxone on opioids is highly dependent not only on host factors, but also on the type of opioid used and the dose used. Each opiate has different characteristics that include the p binding affinity and the lipophilicity.

There are host factors that affect the metabolism of the opioids that impact naloxone's ability to antagonize or reverse their central nervous system manifestations. For example, the genetically polymorphic CYP2D6 is a gene that encodes for the hepatic enzyme P450 2D6. Its expression plays a role in metabolizing most opioids and has been hypothesized to play a role in inter-individual response to opioids. Additionally, variants in the gene encoding for p opioid receptor may alter substrate binding or gene function impacting on opioid metabolism.

In some embodiments, there may be different pharmacokinetic handling of naloxone in opiate dependent versus non-opiate dependent individuals. In animals, an inverse relationship was observed between physical dependence and the amount of naloxone required to elicit withdrawal jumping in mice. Additionally, initial plasma concentration of naloxone can be 20% higher in narcotic free subjects.

In some embodiments, the dose of naloxone required for reversal can be compared to the dose of three opioids (morphine, levorphanol, and pentazocine). In some embodiments, the higher the dose of the opioid agonist administered, the greater the dose of the naloxone needed to reverse the opioid effects on the CNS (particularly respiratory depression). The doses of opiates in the current era of synthetic opioids can be very high and may reach levels which result in rapid respiratory depression and death. High systemic levels of fentanyl found in overdoses can require higher doses of naloxone to adequately compete at opiate receptor binding sites.

One of the major concerns of naloxone treatment of opioid overdose is acute opioid withdrawal syndrome (OWS). The clinical effects observed in OWS due to excessive or overlay rapid reversal of opioid overdose includes vomiting, seizure, delirium, and agitation. Although uncommon, life threatening hemodynamic adverse events thought to be due to a surge on OWS can occur, including hypertensive emergency, acute respiratory distress syndrome, ventricular tachycardia, ventricular fibrillation, and sudden death.

In some embodiments, for self or layperson administration, there may only be one chance to reverse the effects of the more potent opiates, such as fentanyl. Thus, the compositions and methods described herein can be administered in a single injection. However, in some embodiments, multiple injections can be administered.

In some embodiments, incidence of OWS in new synthetic opioid cases can require multiple doses of naloxone. Thus, the risk may be low of OWS by increasing the naloxone doses/levels.

Morphine has different receptor binding and lipophilicity profiles compared to fentanyl (see Table 1). However, morphine has similar receptor binding affinity (1.168 nM) to the p receptor compared with fentanyl (1.346 nM). However, fentanyl (4.28 log P) is more lipophilic than morphine (1.07 log P). In some embodiments, the analgesic onset of intravenous (IV) morphine is 6 minutes with a duration of 96 minutes. In contrast, due to its lipophilicity, fentanyl's relative onset for IV administration is 2 minutes with a duration of action of less than 10 minutes. In some embodiments, the greater lipophilicity of fentanyl can be a significant factor in supporting the need for higher doses of naloxone in in treating fentanyl overdoses.

TABLE 1

Differences between Fentanyl and Morphine-
Fentanyl is more lipophilic than morphine

|  | Morphine | Fentanyl |
| --- | --- | --- |
| Receptor Binding | Similar to fentanyl | Similar to morphine |
| Lipophilicity | Lower than fentanyl | Higher than morphine |
| Onset of action | Slower | Faster |
| Duration of action | Longer | Shorter |

Fentanyl was first synthesized in 1960 by the Belgian company Janssen Pharmaceuticals in a search for an effective rapid-acting analgesic with high potency. At the time, fentanyl was 100 to 200 times more potent than morphine in animal models. In addition, fentanyl had the fastest onset of action, and the highest therapeutic index. Morphine is usually thought of as a long acting analgesic while fentanyl is considered short acting. Because morphine is not very lipid soluble, it takes a longer period of time to cross into the cellular lipid barrier of the brain (blood brain barrier). Thus, morphine's onset is longer. Morphine has a longer duration of action compared to fentanyl due to the longer time exiting the CNS. Fentanyl and morphine have similar affinities for the p receptor (1.346 uM and 1.168 uM respectively). The longer duration and onset of morphine can be "slow in slow out" in contrast to fentanyl, which can be "fast in fast out" (see table 1).

Fentanyl and heroin injections have very similar half-life's (3-7 hours). However, in the CNS, heroin is converted to morphine which is less lipophilic and is retained in the CNS for a longer duration of action like morphine. Fentanyl, in contrast, is persistently lipophilic and thus has a shorter duration (30-60 minutes) due to its rapid exit from the CNS.

The onset of fentanyl and peak plasma levels can also be dependent on the dosage and the type of delivery. Analgesia can occur within minutes of an intravenous delivery in contrast to intranasal delivery which takes 5 to 10 minutes for pain relief. The half-life of fentanyl is not consistent with its rapid and short duration of action due to its persistent lipophilicity in the CNS. Analgesia may be achieved with plasma levels of Fentanyl as low as 0.2 ng/mL in opioid naïve patients, but higher levels may be needed in opioid tolerant patients since fentanyl is metabolized by the cytochrome P450 system. Interactions can occur when used concomitantly with drugs that effect this isoenzyme system.

Fentanyl has become one of the most widely used opioids for the management of pain and is available for administration intravenously, transdermally and transmucosally. Fentanyl, like morphine and other opioids, produces fatigue, sedation, nausea, vomiting, dizziness, bradycardia, respiratory depression, apnea, unconsciousness and death at higher doses due to p opioid receptor stimulation. Numerous analogues of fentanyl have been synthesized, including carfentanil and lofentanil, which can be 100 times more potent than fentanyl.

A major source of illicit fentanyl in the United States and Canada comes from laboratories in China. Fentanyl is also manufactured illegally in Mexico and smuggled into the United States. Illicit fentanyl is made into different forms including powder for injection, smoking, inhalation and tablets. Fentanyl can be mixed with heroin or cocaine to increase its potency. It can also be mixed in tablets with oxycodone or alprazalom. Fatal systemic blood levels of fentanyl can range from 0.5 to 162 ng/mL. The reported EC50 (half maximum effective concentration) values for respiratory suppression with fentanyl can be 3.5±1.4 ng/mL. High doses have been appreciated in the synthetic opioid era.

Morphine and buprenorphine are indeed different than fentanyl, which has greater lipophilicity.

In some embodiments, multiple doses of naloxone can be administered in order to achieve reversal. For example, emergency medical providers from 2012 to 2015 found that the percentage of patients receiving multiple naloxone treatments increased from 14.5% to 18.2% in 2015. Another study examined the incidence of naloxone redosing in New Jersey Emergency Medical system from 2014-2016. This study suggested that the incidence of requiring a second dose of naloxone in response to an opioid overdose was 9%, with a 2.4% rate requiring a third dose. A further study looked at emergency department patients with opioid overdoses from 2016-2017 and found that the total number of naloxone doses was variable with a median from 4 to 8 doses required. In some embodiments, a significant negative correlation exists between dose and age with higher does required in younger patients 20-30 years of age. A further study reported characteristics of fentanyl overdose in Massachusetts from 2014-2016. This study reported 83% of patients required greater than 2 naloxone doses (usually nasal 2 mg/2 mL) in suspected fentanyl cases before a response was observed.

In some embodiments, the use of multiple naloxone doses can be due to the widespread misuse of fentanyl and its greater penetration into the CNS.

In some embodiments, re-narconization can result with some opioids requiring additional doses of naloxone due to their longer duration of action. However, fentanyl has a short duration of action and the studies documenting re-dosing have failed to report re-narconization. Therefore, a need for re-dosing of naloxone may be due to the need for higher doses to compete with the higher doses and distribution of the fentanyl, rather than re-narconization.

In some embodiments, higher doses of naloxone may provide a reasonable balance between therapeutic reversal effects and withdrawal symptoms.

In some embodiments, the naloxone compositions described herein can combat this new era of overdoses. This need can be related to the qualitative and quantitative characteristics of fentanyl and its analogues. Overdoses from fentanyl and its analogues may result in serious morbidity and mortality. Thus, higher doses of naloxone, as descried herein, are needed in the current shifting epidemic.

Fentanyl differs from other opiates as having a very rapid onset and transport out of the CNS. Fentanyl can therefore be widely distributed in the CNS. Furthermore, a high range of systemic levels of fentanyl have been observed in overdose victims.

Figure 9:
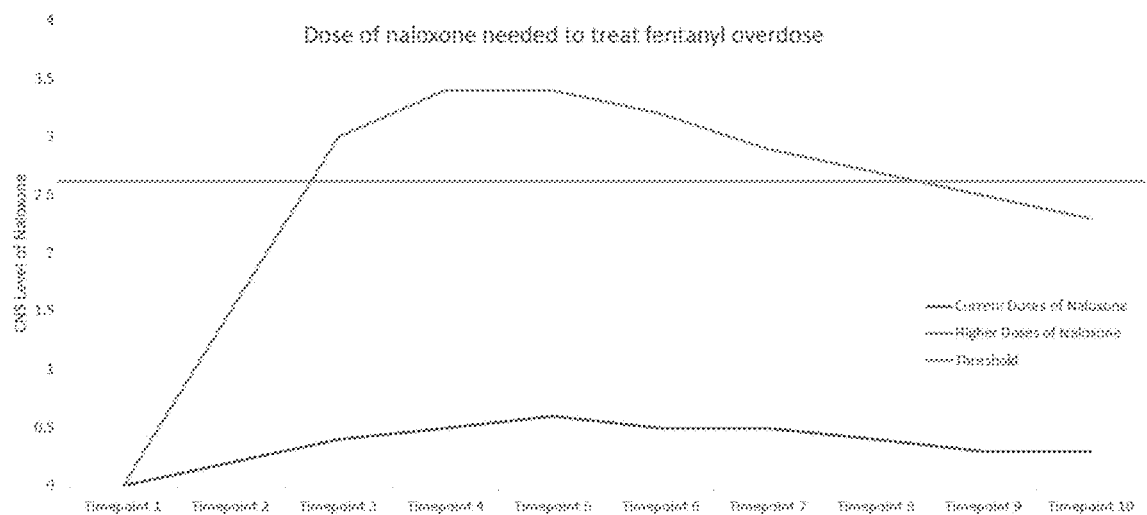
FIG. 9 illustrates hypothetical CNS concentrations of naloxone required in the new opioid era—a threshold of naloxone may be required in the CNS to compete with larger number of bound opiate receptors with fentanyl.
Figure 10:
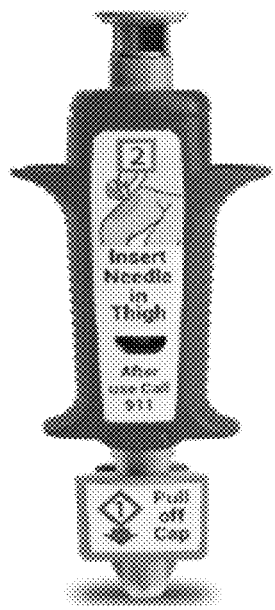
FIG. 10 illustrates an example syringe system used to administer the high dose naloxone.

In some embodiments, high dose naloxone compositions, as described herein, can be used to exceed threshold concentrations of fentanyl at the p opioid receptor level in the CNS. This situation can be illustrated by FIG. 9.

Because re-dosing for lay or self-administration may not be feasible, some embodiments include administering high doses of naloxone. This may be a simple countermeasure that can be initiated rapidly in an attempt to lower morbidity and mortality.

Methods of treatment can include injecting a composition including a high dose of naloxone to a mammal experiencing an opioid overdose.

Methods of treatment can include intramuscularly injecting a composition including a high dose of naloxone to a mammal experiencing an opioid overdose.

Administration can be by one, two, three, four, five, six, seven, eight, nine, ten, or more injections of high dose naloxone. In one embodiment, administration is by one injection.

Other methods of treatment can include administering by inhalation a composition including a high dose of naloxone to a mammal experiencing an opioid overdose.

Other methods of treatment can include administering by inhalation a composition including a high dose of naloxone to a mammal experiencing an opioid overdose.

Associated with dramatic increase in synthetic opioid abuse, the present compositions can in some embodiments, prevent the need for frequent re-dosing.

In the current opioid epidemic, the abuse of more potent opioids such as synthetic fentanyl may result in less effective treatment using the currently approved naloxone products. Higher doses may be more efficacious. Fentanyl is indeed a lipophilic molecule and has the ability to more rapidly saturate the μ opioid receptors compared to morphine.

Naloxone hydrochloride is usually given intravenously for the most rapid action, with onset within 2 minutes. The onset of action is only slightly less rapid when it is given intramuscularly or subcutaneously. Other routes, including nasal and endotracheal, have also been used. The duration of action of naloxone is dependent on the dose and route, but is generally in the range of 1 to 4 hours.

Higher doses of an intramuscular injection, as described here, may result in a higher maximum observed plasma concentration ($C_{max}$) and area under the plasma concentration-time curve (AUC). These pharmacokinetic (PK) characteristics can be desirable for a product in the current opioid epidemic characterized by more potent opioid analogs. Currently, the highest doses of naloxone which are available for self-administration are 2-mg intramuscular (EVZIO) and 4-mg intranasal product (Narcan). These two products are essentially equivalent in terms of bioavailability (Narcan SBA) with some differences; the intramuscular route can result in a faster $T_{max}$ (0.25 hours [intramuscular] compared to 0.5 hours [intranasal]) and a higher $C_{max}$ (7.91 ng/mL [intramuscular] compared to 4.83 ng/mL [intranasal]). Therefore, higher doses given by intramuscular route may have advantages compared to other routes of delivery.

A comparison of even higher doses of naloxone reveals that 5 mg intramuscular naloxone results in a higher $C_{max}$ and AUC than 8 mg intranasal naloxone. For example, 8 mg intranasal naloxone results in a $C_{max}$ of 10.3 ng/mL whereas 5 mg intramuscular naloxone results in a higher $C_{max}$ of 15.8 ng/mL. This demonstrates that 5 mg intramuscular naloxone is more effective in treating an opioid overdose than 8 mg intranasal naloxone. Therefore, lower doses of naloxone given by intramuscular route compared to higher doses of naloxone given by intranasal route are more effective in treating an opioid overdose.

The following represent non-limiting embodiments.

Embodiment 1: An emergency syringe device comprising a syringe including a therapeutic dose of at least one opioid antagonist, and a stopper; and a plunger assembly including a plunger rod, an actuator, and a spacer, wherein the plunger assembly is configured to move the stopper a predetermined distance without a user touching the plunger rod or being able to retract the plunger rod.

Embodiment 2: The syringe device of Embodiment 1, wherein the plunger assembly is configured to provide substantially identical doses of the at least one opioid antagonist even if more or less opioid antagonist is provided in the syringe by moving the stopper a predetermined distance.

Embodiment 3: The syringe device of Embodiment 1 or 2, further including an encasement configured to house the syringe.

Embodiment 4: The syringe device of Embodiment 1, 2, or 3, wherein the encasement includes a window configured to allow the user to view the at least one opioid antagonist in the syringe.

Embodiment 5: The syringe device of Embodiment 1, 2, or 3, wherein the encasement includes a needle guard configured to allow the user to cover the needle after use.

Embodiment 6: The syringe device of Embodiment 1, 2, 3, 4, or 5, wherein the at least one opioid antagonist is naloxone, a salt thereof, a derivative thereof, or a prodrug thereof.

Embodiment 7: The syringe device of Embodiment 1, 2, 3, 4, 5, or 6, wherein the at least one opioid antagonist is naloxone.

Embodiment 8: The syringe device of Embodiment 1, 2, 3, 4, 5, 6, or 7, wherein the syringe device is configured to deliver about 5 mg of naloxone or a salt thereof.

Embodiment 9: The syringe device of Embodiment 1, 2, 3, 4, 5, 6, or 7, wherein the syringe device is configured to deliver about 15 mg of naloxone or a salt thereof.

Embodiment 10: The syringe device of Embodiment 1, 2, 3, 4, 5, 6, 7, 8, or 9, wherein the actuator and the spacer are configured to be secured around the plunger rod.

Embodiment 11: The syringe device of Embodiment 1, 2, 3, 4, 5, 6, 7, 8, 9, or 10, wherein the actuator includes a finger depression location.

Embodiment 12: The syringe device of Embodiment 1, 2, 3, 4, 5, 6, 7, 8, 9, 10, or 11 configured for use in an opioid overdose.

Embodiment 13: A method for administering a therapeutic dose of at least one opioid antagonist, the method comprising advancing a stopper through a syringe including the therapeutic dose of the at least one opioid antagonist; wherein the stopper is only advanced a predetermined distance by a plunger assembly including a plunger rod, an actuator, and a spacer, wherein the plunger assembly is configured to move the stopper without a user touching the plunger rod.

Embodiment 14: The method of Embodiment 13, wherein the syringe is housed in an encasement.

Embodiment 15: The method of Embodiment 13 or 14, wherein the encasement includes a window configured to allow the user to view the at least one opioid antagonist in the syringe.

Embodiment 16: The method of Embodiment 13 or 14, wherein the encasement includes a needle guard configured to allow the user to cover a needle after use.

Embodiment 17: The method of Embodiment 13, 14, 15, or 16, wherein the at least one opioid antagonist is naloxone, a salt thereof, a derivative thereof, or a prodrug thereof.

Embodiment 18: The method of Embodiment 13, 14, 15, 16, or 17, wherein the at least one opioid antagonist is naloxone.

Embodiment 19: The method of Embodiment 13, 14, 15, 16, 17, or 18, wherein the actuator and the spacer are configured to be secured around the plunger rod and provide the predetermined distance.

Embodiment 20: The method of Embodiment 13, 14, 15, 16, 17, 18, or 19, wherein the actuator and the spacer are configured to provide the predetermined distance between a start point and an end point.

Embodiment 21: The method of Embodiment 13, 14, 15, 16, 17, 18, 19, or 20, wherein the advancing the stopper the predetermined distance is configured to deliver about 5 mg of naloxone or a salt thereof.

Embodiment 22: The method of Embodiment 13, 14, 15, 16, 17, 18, 19, 20, or 21, wherein the advancing the stopper the predetermined distance is configured to deliver about 15 mg of naloxone or a salt thereof.

Example 1

Emergency Naloxone Administration

A 45 year old female suffers from frequent heroin use. After injecting a large dose of heroin intravenously at a party, the female begins to show symptoms of overdose and becomes unconscious. Her heart rate slows and her breath becomes shallow. An onlooker at the party calls 911. The onlooker finds a kit of two naloxone filled syringe devices housed in separate connected cases stocked in the locations first aid kit. He opens one case and removes the syringe device.

An injection area is determined on the female's thigh. He removes the needle cap, inserts the needle into the female's thigh in the selected area, and pushes the plunger until he hears a click. He leaves the needle in the female's thigh for an additional two seconds. He then removes the needle from the female's thigh, slides down the needle cap, places the syringe device back in the container, and shuts the container.

The female slowly regains consciousness. Medical emergency personnel arrive shortly thereafter and transport the female to a local emergency room for further treatment.

Example 2

Emergency Naloxone Aided Injection

A 65 year old man is depressed and ingests a bottle of prescription opioids, thus overdosing himself. The man's wife finds the man barely conscious. The wife calls 911 while she pulls out a kit of two naloxone filled syringe devices housed in separate connected cases. She pops open one case and removes the syringe device.

She selects an injection area on the man's thigh. She removes the needle cap, inserts the needle into the man's thigh in the selected area, and pushes the plunger until she hears a click. She then removes the needle from the man's thigh, slides down the needle cap, places the syringe device back in the container, and shuts the container.

She notices that the injection has little effect on the man. Thus, she pops open the second case and removes the syringe device inside. She repeats injection with the second device. She again removes the needle from the man's thigh, slides down the needle cap, places the syringe device back in the container, and shuts the container.

The man slowly regains consciousness. Medical emergency personnel arrive shortly thereafter and transport the man to a local emergency room for further treatment.

Example 3

In Example 1 and Example 2, each syringe in the kit includes 5 mg of naloxone.

Example 4

In Example 1 and Example 2, each syringe in the kit includes 2.5 mg of naloxone.

Example 5

In Example 1 and Example 2, each syringe in the kit includes 10 mg of naloxone.

Example 6

In Example 1 and Example 2, each syringe in the kit includes 15 mg of naloxone.

Example 7

An open-label, randomized, single-dose, 2-period, 2 treatment crossover bioavailability study was performed to evaluate the safety and bioavailability of 5 mg/0.5 mL intramuscular naloxone hydrochloride to 2 mg/0.4 mL intramuscular naloxone hydrochloride auto-injector (EVZIO®, Kaleo, Inc.) in healthy subjects. Fourteen male and female subjects 18 to 55 years of age (inclusive) were enrolled in the study to ensure that at least 12 subjects completed the study. The subjects selected had a body mass index (BMI) between 18 and 33 kg/m$^2$ and a total body weight of >45 kg. Participation in the study was voluntary and each subject had the right to discontinue participation at any moment.

This study consisted of a screening visit (up to 28 days before the first dosing period) and 2 study periods (each separated by a minimum of 48 hours). Subjects reported to the Clinical Research Unit (CRU) on Day 1 (check-in) and remained at the CRU for 5 days (approximately 12 hours after Period 2 Day 4). Subjects were randomized to 1 of 2 treatment sequences and the following treatments were administered on Day 1 of each study period: Treatment A—5 mg/0.5 mL intramuscular naloxone hydrochloride (test), or Treatment B—2 mg/0.4 mL intramuscular naloxone hydrochloride auto-injector (reference). All doses were administered into the anterolateral aspect of the thigh.

Subjects were required to fast (no food or drink other than water) for 4 hours after dosing; water was allowed ad libitum after the first hour after dosing. Subjects refrained from lying down for 4 hours after dosing (except when required for vital signs and ECG measurements).

For each subject, the following PK parameters were calculated, whenever possible, from plasma concentrations of naloxone hydrochloride using standard non-compartmental methods: maximum observed plasma concentration ($C_{max}$), time of maximum observed plasma concentration ($T_{max}$), time of last quantifiable plasma concentration ($T_{last}$), area under the plasma concentration-time curve (AUC) from time 0 to the time of the last measurable plasma concentration ($AUC_{0-t}$), AUC from time 0 extrapolated to infinity ($AUC_{0-inf}$), percentage of AUC that is due to extrapolation from the last measurable plasma concentration to infinity (% $AUC_{extrap}$), apparent terminal elimination rate constant ($\lambda_z$), apparent plasma terminal elimination half-life ($t_{1/2}$), apparent total plasma clearance (CL/F), apparent volume of distribution during the terminal elimination phase ($V_z/F$).

Safety was assessed throughout the study by AE monitoring, clinical laboratory tests, ECGs, continuous cardiac monitoring, physical examination, and vital sign monitoring.

Higher doses using a prefilled syringe were used in this study. The clinical rational was based on the current epidemiology of more potent opioid analogs and some cases of limited effectiveness of the available naloxone products. The 2 mg/0.4 mL naloxone hydrochloride in auto-injectors (lot numbers: F0127017BB, F0122917BB, and F0126217BB) were supplied by Kaleo, Inc. and the 5 mg/0.5 mL naloxone hydrochloride (lot numbers 01-24apr.2018-829 and 02-26apr.2018-829) was supplied and prepared by Covance. Study treatments were stored at ambient/room temperature (between 15° C. and 30° C.) under secure conditions.

The concept that higher doses are needed is further supported by studies that have shown that the degree of reversal from morphine effects, such as respiratory depression, is dose dependent up to 10 mg. In addition, most of the literature supports naloxone dose up to 10 mg as being safe.

Of note, a package insert for naloxone notes a small adult study where 24 mg/70 kg of naloxone was given to human volunteers without toxicity.

More recently, a study suggested that more concentrated doses of a nasal naloxone at 8 and 16 mg demonstrated higher AUC, $T_{max}$, and $C_{max}$ in a dose dependent manner. These doses were also shown to be well tolerated and safe in the study.

During the study, subjects abstained from all concomitant medications (prescription or nonprescription drugs and dietary supplements). As an exception, acetaminophen/paracetamol may have been used at doses of ≤1 g/day, and hormonal contraceptives or hormone replacement therapy was allowed in female subjects. Iron supplements may have been provided as needed. Subjects refrained from participation in any other investigational study drug or device trial in which receipt of any investigational drug occurred within 5 half-lives (if known) or 30 days, whichever was longer, prior to dosing. Use of prescription or nonprescription drugs and dietary supplements within 7 days or 5 half-lives (whichever is longer) prior to the first dose of study medication was prohibited. Herbal supplements were discontinued at least 28 days prior to the first dose of study medication. Medications taken within 28 days before the first dose of study medication were documented as prior medications. Medications taken after the first dose of study medication were documented as concomitant medications.

All doses were prepared and administered by qualified clinical site staff.

Subjects were required to abstain from consuming alcohol, grapefruit, and Seville orange-containing foods and beverages for 72 hours prior to dosing. Subjects were also prohibited from consuming caffeine within 1 hour prior to dosing and for 2 hours after dosing. While confined at the clinical site, subjects received a standardized diet at scheduled times that did not conflict with other study-related activities.

Subjects were prohibited from consuming nicotine-containing products within 1 hour prior to dosing and for 2 hours after dosing.

Subjects abstained from strenuous exercise (eg, heavy lifting, weight training, calisthenics, and aerobics) for at least 5 days prior to each blood collection for clinical laboratory tests. Walking at a normal pace was permitted.

Following a single intramuscular dose of naloxone hydrochloride administered as 5 mg/0.5 mL (Treatment A, Test), absorption was rapid with a median $T_{max}$ of 0.31 hours with individual values ranging from 0.08 to 0.55 hours. After reaching $C_{max}$ (arithmetic mean [SD] of 16.5 ng/mL [8.03]), plasma concentrations declined in an apparent biphasic manner. The arithmetic mean $t_{1/2}$ was 1.60 hours with values for individual subjects ranging from 1.00 to 1.97 hours.

Following a single intramuscular dose of naloxone hydrochloride administered as 2 mg/0.4 mL via an auto-injector (Treatment B, Reference), absorption was rapid with a similar median $T_{max}$ of 0.28 hours with individual values ranging from 0.08 to 0.58 hours. After reaching $C_{max}$ (arithmetic mean [SD] of 4.63 ng/mL 1.57]) plasma concentrations declined in an apparent biphasic manner. The arithmetic mean $t_{1/2}$ was 1.47 hours with values for individual subjects ranging from 0.80 to 1.94 hours.

When comparing the test versus reference groups, apparent total plasma clearance (CL/F) showed a slight increase as the dose was reduced with a geometric mean of 3970 mL/min for the 5 mg/0.5 mL (Treatment A, Test) group and 4350 mL/min for the 2 mg/0.4 mL (Treatment B, Reference) group.

The PK results showed administration of higher doses of intramuscular naloxone hydrochloride (5 mg/0.5 mL [Test] compared to 2 mg/0.4 mL [Reference]) did increased both $C_{max}$ and AUCs and slight increases were also noted for $t_{1/2}$. However, $T_{max}$ was similar for both treatments. Statistical analysis indicated that there were statistical differences between the test and reference treatments for $C_{max}$, AUCs, and $t_{1/2}$ with ratios of test to reference for $C_{max}$ of 337.1% (CI: 263.3%, 431.5%), $AUC_{0-t}$ of 277.5% (CI: 260.4%, 295.7%), $AUC_{0-inf}$ of 273.4% (CI: 255.6%, 292.4%), and $t_{1/2}$ of 110.5% (CI: 95.5%, 127.9%). This results show that higher doses of intramuscular naloxone hydrochloride result in higher $C_{max}$ and AUCs and these PK characteristics are desirable for a product intended to be used to reverse overdose reactions caused by the higher potency of abused opioids.

Statistical analysis of the PK parameters showed that the overall extent of absorption ($C_{max}$ and AUCs) and the disposition kinetics of naloxone hydrochloride administered as either a 5 mg/0.5 mL (Treatment A, Test) or 2 mg/0.4 mL via an auto-injector (Treatment B, Reference) increased for the 5 mg/0.5 mL (Test) group compared to the 2 mg/0.4 mL (Reference) group with ratio of test to reference for $AUC_{0-t}$ of 277.5% (CI: 260.4%, 295.7%), $AUC_{0-inf}$ of 273.4% (CI: 255.6%, 292.4%), and $C_{max}$ of 337.1% (CI: 263.3%, 431.5%). These $C_{max}$ and AUCs CIs were outside the standard 80% to 125% CI range for bioavailability. Half-life was slightly increased with ratio of test to reference of 110.5% (CI: 95.5%, 127.9%) with the upper bound of the CI greater than 125%. Statistical analysis indicates that $T_{max}$ was similar for the 5 mg/0.5 mL (Test) group and the 2 mg/0.4 mL (Reference) group at 0.31 hours and 0.28 hours, respectively. These pharmacokinetic parameters and statistics are shown below in Table 2:

TABLE 2

Statistical Analysis of the Bioavailability between Test and Reference Treatments of Intramuscular Naloxone Hydrochloride

| PK Parameters | Treatment A (Test) | | Treatment B (Reference) | | Ratio of Test/Reference[c] (%) | 90% CI[d] of Test/Reference (%) |
|---|---|---|---|---|---|---|
| | n[a] | LS Mean[b] | n[a] | LS Mean[b] | | |
| $C_{max}$ (ng/mL) | 14 | 14.9 | 14 | 4.41 | 337.1 | (263.3, 431.5) |
| $t_{1/2}$ (h) | 14 | 1.58 | 14 | 1.43 | 110.5 | (95.5, 127.9) |
| $T_{max}$ (h) # | 14 | 0.308 | 14 | 0.283 | 0.017 | (−0.1, 0.1) |

TABLE 2-continued

Statistical Analysis of the Bioavailability between Test
and Reference Treatments of Intramuscular Naloxone Hydrochloride

| PK Parameters | Treatment A (Test) | | Treatment B (Reference) | | Ratio of Test/Reference[c] (%) | 90% CI[d] of Test/Reference (%) |
|---|---|---|---|---|---|---|
| | n[a] | LS Mean[b] | n[a] | LS Mean[b] | | |
| $AUC_{0-t}$ (h * ng/mL) | 14 | 20.6 | 14 | 7.42 | 277.5 | (260.4, 295.7) |
| $AUC_{0-inf}$ (h * ng/mL) | 14 | 21.0 | 14 | 7.67 | 273.4 | (255.6, 292.4) |

Treatment A: 5 mg/0.5 mL intramuscular naloxone hydrochloride (Test)
Treatment B: 2 mg/0.4 mL intramuscular naloxone hydrochloride auto-injector (Reference)
Abbreviations:
CI = confidence interval;
LS = least square.
[a]n was the number of observations.
[b]Least-squares (LS) mean from ANOVA, calculated by transforming the natural-log mean back to the linear scale (ie, geometric mean).
[c]Ratio of parameter LS means for natural log-transformed parameter. Natural log-transformed ratios transformed back to the linear scale (expressed as a percentage).
[d]90% confidence interval for ratio of parameter LS means of natural log-transformed parameter. Natural log-transformed confidence limits transformed back to the linear scale (expressed as a percentage).
Medians, median of differences, approximate 90% confidence interval from the Wilcoxon signed rank test are presented.
Reference: Table 14.2.1-1
Program Location: /cvn/projects/prj/ecb/programs/000000159685/dev/tables/t_stat_ba.sas
Program Run: 15OCT2018 cvn_ngeng Program Status: FINAL Sponsor Reference: APC6000-01

Figure 11:
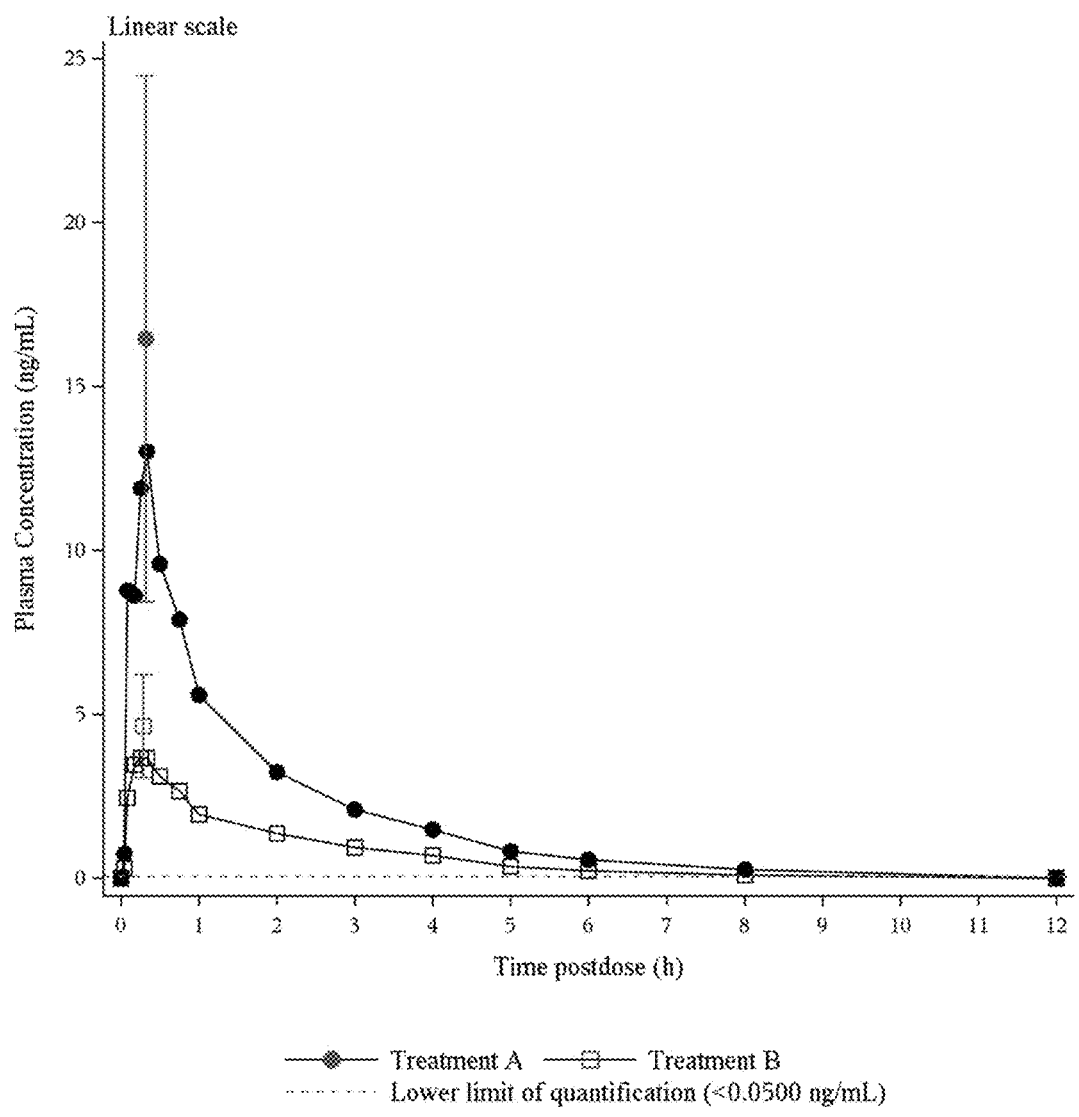
FIG. 11 illustrates preliminary results of a pharmacokinetic (PK) study comparing 5 mg versus 2 mg intramuscular injection over 12 hours.
Figure 12:
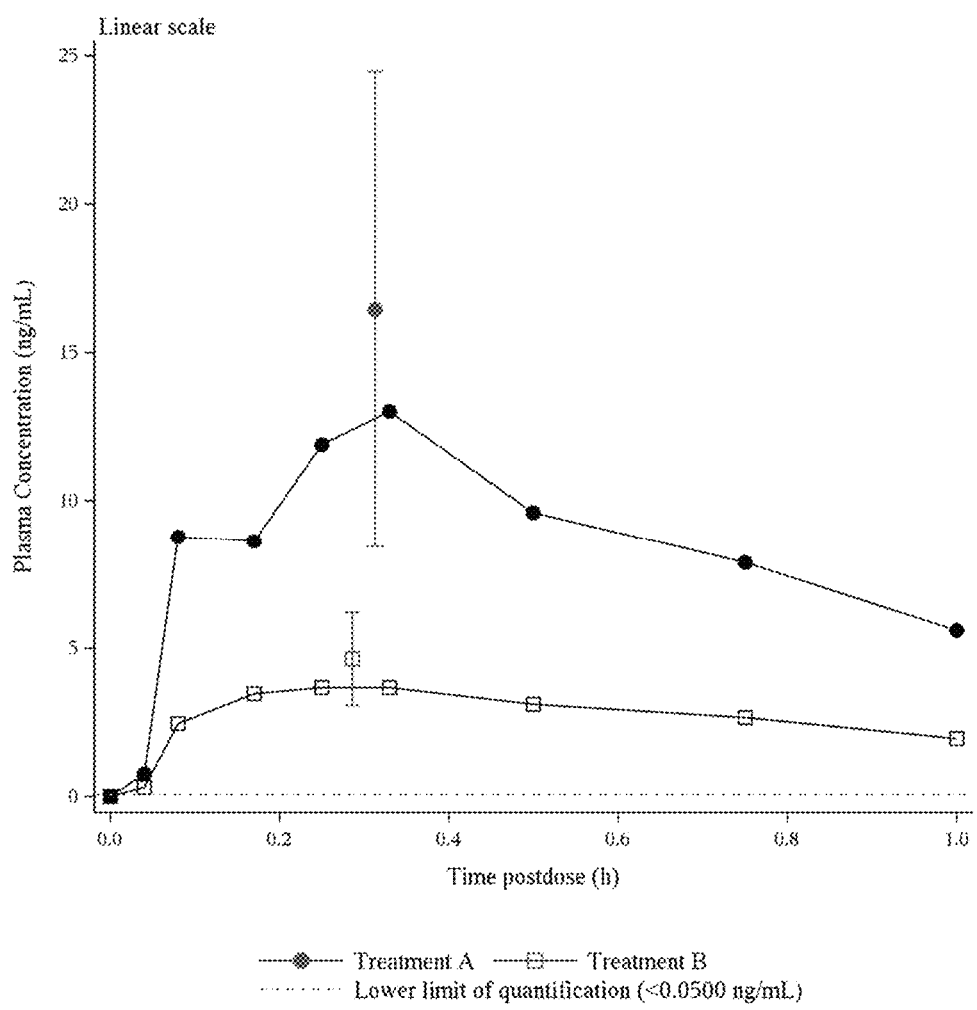
FIG. 12 illustrates preliminary results of a PK study comparing 5 mg versus 2 mg intramuscular injection over the first hour after injection.

The mean concentration over the first 12 hours is shown in FIG. 11. The mean concentration between the two groups over the first hour is shown in FIG. 12. It is reasonable likely that systemic levels of naloxone cross the blood brain barrier and are able to compete more opiate receptors. These data suggest the potential to address an unmet medical need particularly for treatment of opioid overdoses due to the more potent synthetic opioids.

In general, as assessed from the geometric CV %, low between-subject variability was noted from $AUC_{0-inf}$ for both formulations with values ranging from 15.4% to 14.2% for the 5 mg/0.5 mL (Test) group compared to the 2 mg/0.4 mL (Reference) group, respectively; while the between-subject-variability for both formulations was moderate for $C_{max}$ with CV % values ranging from 48.5% to 33.1% for the 5 mg/0.5 mL (Test) group compared to the 2 mg/0.4 mL (Reference) group, respectively.

The plasma concentration versus time profiles for both the 5 mg/0.5 mL (test) and 2 mg/0.4 mL (reference) formulations were characterized by a rapid absorption phase, with a higher arithmetic mean $C_{max}$ (SD) being attained in the 5 mg/0.5 mL (Test) group (16.5 ng/mL [8.03]) compared to the 2 mg/0.4 mL (Reference) group (4.63 ng/mL [1.57]).

No significant difference in $T_{max}$ was noted between the groups, with median values of 0.31 hours and 0.28 hours, respectively, for the 5 mg/0.5 mL (Test) group and the 2 mg/0.4 mL (Reference) group.

Overall, naloxone hydrochloride was safe and well tolerated when administered as either the 5 mg/0.5 mL intramuscular naloxone hydrochloride or 2 mg/0.4 mL intramuscular naloxone hydrochloride auto-injector (EVZIO, Kaleo, Inc.) formulation. During the study, no deaths, other serious adverse events (SAEs), or (adverse events) AEs were reported. Also, there were no safety laboratory abnormalities, vital sign measurements, or ECG findings reported as an AE during this study. Additionally, there were no clinically significant changes or findings in physical examinations for this study.

Example 8

Another study investigated the higher doses of naloxone HCl. The clinical rational is based on the current epidemiology of more potent opioid analogues and some cases of limited effectiveness of the available naloxone products. Previous studies indicate that multiple doses of the currently approved products are needed to reverse opioid overdoses, and in some cases, is still insufficient due to the use of more potent opioid analogues such as synthetic fentanyl.

This study was a Phase I, open-label, randomized, single-dose, 2-period, 2-treatment crossover bioavailability study comparing 5 mg/0.5 mL of intramuscular naloxone HCl to 2 mg/2 mL intramuscular naloxone HCl injection (1 mg/1 mL, International Medical Systems) in healthy subjects. The primary objective of this study was to compare bioavailability of intramuscular naloxone HCl 5 mg/0.5 mL to 2 mg/2 mL intramuscular naloxone HCl injection (1 mg/1 mL, International Medical Systems) in healthy subjects. The secondary objective of the study was to assess the safety and tolerability during the course of the study. A total of 14 subjects participated in the study and all subjects completed the study. Overall, the intramuscular injection of naloxone HCl was well-tolerated when administered as either the 5 mg/0.5 mL or 2 mg/2 mL (1 mg/1 mL, International Medical Systems) formulation.

Fourteen healthy male and female subjects 18 to 55 years of age (inclusive) were enrolled in the study. Subjects had a body mass index (BMI) between 18 and 32 kg/m² and a total body weight of >45 kg. Participation in the study was strictly voluntary. Each subject had the right to discontinue participation in the study at any moment, for any reason.

The study incorporated a screening visit (up to 28 days before the first dosing period) and 2 study periods (each separated by a minimum of 48 hours).

Subjects remained confined at the study site for 5 days: from Day −1 (one day prior to study drug administration) until approximately 12 hours after the completion of the 2 study periods (Day 4). Subjects were randomized to 1 of 2 treatment sequences; the following treatments were administered on Day 1 of each study period: Treatment A: 5 mg naloxone HCl administered as 5 mg/0.5 mL naloxone HCl for injection packaged in a single-use prefilled syringe in a delivery device (test product) or Treatment B: 2 mg naloxone HCl administered as 2 mg/2 mL intramuscular naloxone HCl injection (1 mg/1 mL, International Medical Systems) (reference product).

Doses in Period 1 and Period 2 were separated by at least 48 hours. All doses were administered into the anterolateral aspect of the thigh. Subjects were required to fast prior to dosing. Lunch was provided 4 hours after study drug administration. Water was allowed ad libitum after the first hour after dosing. Subjects refrained from lying down for 4 hours after dosing.

The reference drug (2 mg/2 mL naloxone HCl injection) (lot number: RL010B9) was supplied by International Medical Systems. The test product (5 mg/0.5 mL naloxone HCl) (lot number: 19062N) prefilled syringe was manufactured by Siegfried and the device was assembled and supplied by Phillips Medisize on behalf of Adamis Pharmaceuticals.

Study treatments were stored at ambient/room temperature (between 15° C. and 30° C.) under secure conditions.

Safety was assessed throughout the study by AE monitoring, clinical laboratory tests, ECG, physical examination, vital sign monitoring, and continuous cardiac monitoring. Blood samples for PK analysis were collected.

Higher doses of naloxone using a Type 2 prefilled drug delivery device/system was used in this study. The clinical rational was based on the current epidemiology of more potent opioid analogs and some cases of limited effectiveness of the available naloxone products.

During the study, subjects abstained from all concomitant medications (prescription or nonprescription drugs and dietary supplements). As an exception, acetaminophen/paracetamol may have been used at doses of ≤1 g/day, and hormonal contraceptives or hormone replacement therapy was allowed in female subjects. Subjects refrained from participation in any other investigational study drug or device trial in which receipt of any investigational drug occurred within 30 days or 5 half-lives or as determined by the local requirement, whichever was longer, preceding the first dose of study medication.

Use of prescription or nonprescription drugs and dietary supplements within 7 days or 5 half-lives (whichever was longer) prior to the first dose of study medication was prohibited.

Herbal supplements were discontinued at least 28 days prior to the first dose of study medication. As an exception, acetaminophen/paracetamol may have been used at doses of ≤1 g/day; hormonal contraceptives or hormone replacement therapy may be continued in female subjects. Iron supplements may have been provided as needed.

Medications taken within 28 days before the first dose of study medication were documented as prior medications. Medications taken after the first dose of study medication were documented as concomitant medications.

All doses were prepared and administered by qualified clinical site staff.

Subjects fasted for 6 hours prior to dosing on Study Day 1. Subjects were not to consume: alcohol, grapefruit, and Seville oranges or products containing any of these within 72 hour period prior to study drug administration and/or caffeine within the 1-hour period prior to any study drug administration and for 2 hours after dosing.

Subjects received a standardized diet for all meals from Study Day −1 to Discharge. Subjects consumed water on an ad libitum basis throughout the study. No food was allowed up to 4 hours postdose.

Subjects were prohibited from consuming nicotine-containing products within 1 hour prior to dosing and for 2 hours after dosing. Subjects abstained from strenuous exercise (e.g., heavy lifting, weight training, calisthenics, and aerobics) for at least 5 days prior to each blood collection for clinical laboratory tests. Walking at a normal pace was permitted. Subjects refrained from lying down (except when required for vital signs and ECG measurements) during the first 4 hours after each dosing.

No positive predose plasma concentrations of naloxone hydrochloride were observed in any subjects in Periods 1 and 2.

Blood samples for naloxone analyses were collected at 15 minutes prior to dosing (pre-dose, 0 h), at 2.5, 5, 10, 15, 20, 30, and 45 minutes and at 1, 2, 3, 4, 5, 6, 8, and 12 hours postdose.

Following a single intramuscular dose of naloxone HCl administered as 5 mg/0.5 mL (Treatment A, Test), absorption was rapid with a median $T_{max}$ of 0.25 hours with individual values ranging from 0.17 to 0.52 hours. After reaching $C_{max}$ (arithmetic mean [SD] of 17.2 [7.57] ng/mL), plasma concentrations declined in an apparent biphasic manner. The arithmetic mean $t_{1/2}$ was 1.50 hours with values for individual subjects ranging from 1.18 to 1.87 hours.

Following a single intramuscular dose of naloxone hydrochloride administered as 2 mg/2 mL (Treatment B, Reference), absorption was rapid with a similar median $T_{max}$ of 0.25 hours with individual values ranging from 0.05 to 3.00 hours. After reaching $C_{max}$ (arithmetic mean [SD] of 3.58 [2.08] ng/mL) plasma concentrations declined in an apparent biphasic manner. The arithmetic mean $t_{1/2}$ was 1.86 hours with values for individual subjects ranging from 1.18 to 2.64 hours.

When comparing the test versus reference treatments, mean CL/F and apparent volume of distribution during the terminal elimination phase ($V_z/F$) values were similar. Arithmetic mean (SD) CL/F and $V_z/F$ values were 196 (42.9) L/h and 419 (78.3) L after 5 mg/5 mL (Test) and 212 (53.0) L/h and 559 (186) L after 2 mg/2 mL (Reference).

The plasma concentration versus time profiles for both the 5 mg/0.5 mL (Test) and 2 mg/2 mL (Reference) formulations were characterized by rapid absorption, with a higher arithmetic mean $C_{max}$ (SD) being attained after 5 mg/0.5 mL (Test) (17.2 [7.57] ng/mL) compared to 2 mg/2 mL (Reference) (3.58 [2.08] ng/mL). Statistical analysis showed that administration of a higher dose of intramuscular naloxone hydrochloride (5 mg/0.5 mL [Test] compared to 2 mg/2 mL [Reference]) resulted in higher $C_{max}$ and AUCs. Statistical analysis also demonstrated that the higher dose of naloxone (Test) had a significantly greater AUC during the first 2.5 and 5 minutes compared to Reference.

Statistical analysis of the PK parameters showed that the overall extent of absorption ($C_{max}$ and AUCs) of naloxone HCl administered as 5 mg/0.5 mL (Treatment A, Test) or 2 mg/2 mL (Treatment B, Reference) was higher after 5 mg/0.5 mL (Test) compared to 2 mg/2 mL (Reference), with test to reference ratios for $AUC_{0-t}$ of 279.67% (CI: 257.32%, 303.96%), $AUC_{0-inf}$ of 267.63% (CI: 249.14%, 287.49%), and $C_{max}$ of 487.10% (CI: 432.44%, 548.66%). These $C_{max}$ and AUCs CIs were outside the standard 80.00% to 125.00% CI range establishing bioequivalence. For comparison of secondary PK parameters ($AUC_{0-0.04h}$ and $AUC_{0-0.08h}$), statistical analysis showed that early exposure was higher after 5 mg/0.5 mL (Test) group compared to 2 mg/2 mL (Reference), with test-to-reference ratios for $AUC_{0-0.04h}$ of 260.73% (CI: 151.68%, 448.18%) and $AUC_{0-0.08h}$ of 406.26% (CI: 288.61%, 571.89%). Median half-life was slightly longer after 5 mg/0.5 mL (Test) (1.48 h) compared to 2 mg/2 mL (Reference) (1.79 h). Statistical analysis indicated that $T_{max}$ was similar for 5 mg/0.5 mL (Test) and 2 mg/2 mL (Reference); median $T_{max}$ for both treatments occurred at 0.25 h postdose. These pharmacokinetic parameters and statistics are shown below in Table 3:

TABLE 3

Statistical Analysis of the Bioavailability between Test
and Reference Treatments of Intramuscular Naloxone Hydrochloride

| | Treatment A (Test) | | Treatment B (Reference) | | Ratio of Test/Reference[c] | 90% CI[d] of Test/Reference |
|---|---|---|---|---|---|---|
| | n[a] | LS Mean[b] | n[a] | LS Mean[b] | (%) | (%) |
| PK Parameters | | | | | | |
| $C_{max}$ (ng/mL) | 14 | 15.8 | 14 | 3.24 | 487.10 | (432.44, 548.66) |
| $AUC_{0-t}$ (h * ng/mL) | 14 | 25.7 | 14 | 9.18 | 279.67 | (257.32, 303.96) |
| $AUC_{0-inf}$ (h * ng/mL) | 14 | 26.0 | 14 | 9.72 | 267.63 | (249.14, 287.49) |
| Secondary PK Parameters | | | | | | |
| $AUC_{0-0.04h}$ (h * ng/mL) | 14 | 0.0129 | 14 | 0.00496 | 260.73 | (151.68, 448.18) |
| $AUC_{0-0.08h}$ (h * ng/mL) | 14 | 0.0782 | 14 | 0.0192 | 406.26 | (288.61, 571.89) |
| Non-Parametric | | | | | | |
| $T_{max}$ (h) # | 14 | 0.250 | 14 | 0.250 | −0.05 | (−0.17, 0.01) |
| $t_{1/2}$ (h) # | 14 | 1.48 | 14 | 1.79 | −0.31 | (−0.54, −0.13) |

Treatment A = 5 mg/0.5 mL intramuscular naloxone HCl for injection packaged in a single-use prefilled syringe in a delivery device (Test)
Treatment B = 2 mg/2 mL intramuscular naloxone HCl injection (1 mg/1 mL, International Medical Systems (Reference)
Abbreviations:
CI = confidence interval;
LS = least square.
[a] n was the number of observations.
[b] Least-squares (LS) mean from ANOVA, calculated by transforming the natural-log mean back to the linear scale (ie, geometric mean).
[c] Ratio of parameter LS means for natural log-transformed parameter. Natural log-transformed ratios transformed back to the linear scale (expressed as a percentage; ie, geometric mean ratio).
[d] 90% confidence interval for ratio of parameter LS means of natural log-transformed parameter. Natural log-transformed confidence limits transformed
back to the linear scale (expressed as a percentage).
Medians, median of differences, approximate 90% confidence interval from the Wilcoxon signed rank test are presented.
Reference: Table 14.4.3, Table 14.4.4, and Table 14.4.5

TABLE 4

Statistical Analysis of the Natural Log-Transformed Systemic
Exposure Parameters of Naloxone (Primary and Secondary PK Parameters)

| Parameter | Dependent Variable | Geo-Mean[a] Test | Geo-Mean[a] Ref | Ratio (%)[b] (Test/Ref) | 90% CI[c] Lower | 90% CI[c] Upper | p-value[d] | CV %[e] |
|---|---|---|---|---|---|---|---|---|
| Primary | $\ln(C_{max})$ | 15.8 | 3.24 | 487.10 | 432.44 | 548.66 | <0.0001 | 17.81 |
| | $\ln(AUC_{0-t})$ | 25.7 | 9.18 | 279.67 | 257.32 | 303.96 | <0.0001 | 12.41 |
| | $\ln(AUC_{0-inf})$ | 26.0 | 9.72 | 267.63 | 249.14 | 287.49 | <0.0001 | 10.66 |
| Secondary | $\ln(AUC_{0-0.04h})$ | 0.0129 | 0.00496 | 260.73 | 151.68 | 448.18 | 0.0138 | 61.48 |
| | $\ln(AUC_{0-0.08h})$ | 0.0782 | 0.0192 | 406.26 | 288.61 | 571.89 | <0.0001 | 54.21 |

Treatment A = 5 mg/0.5 mL intramuscular naloxone HCl (Test)
Treatment B = 2 mg/2 mL intramuscular naloxone HCl (Reference)
[a] = Geometric Mean based on Least Squares Mean
[b] = Ratio(%) = Geometric Mean (Test)/Geometric Mean (Ref)
[c] = 90% Confidence Interval
[d] = p-value for the difference in the treatment_id estimates; Significant difference defined *a priori* as p <0.05
[e] = Intra-subject variability In general, as assessed from the geometric CV %, low between-subject variability was noted for $AUC_{0-inf}$ for both formulations, with values ranging from 21.5% to 25.0%. The between-subject-variability was moderate for $C_{max}$, with geometric CV % values ranging from 43.2% to 43.9%. Estimates of within-subject variability were low across primary PK parameters, ranging from 10.66% to 17.81%.

No significant difference in $T_{max}$ was noted, with a median $T_{max}$ of 0.25 hours reported for both treatments. A significant difference in $t_{1/2}$ was observed, with median $t_{1/2}$ of 1.48 hours and 1.79 hours for 5 mg/0.5 mL (Test) and 2 mg/2 mL (Reference), respectively. There were no serious SAEs or AEs that led to a subject withdrawal or death.

During the study, no deaths, other SAEs, or AEs were reported. There were no clinically significant events based on vital signs, ECGs, or physical examinations.

The PK results showed that administration of a higher dose of intramuscular naloxone hydrochloride resulted in higher naloxone exposure ($C_{max}$ and AUCs); however, $T_{max}$ occurred at 0.25 hours for both treatments. Statistical analysis indicated that there were significant differences in $C_{max}$ and AUCs between the test and reference treatments, with test to reference ratios for $AUC_{0-t}$ of 279.67% (CI: 257.32%, 303.96%), $AUC_{0-inf}$ 267.63% (CI: 249.14%, 287.49%), and $C_{max}$ of 487.10% (CI: 432.44%, 548.66%). For comparison of secondary PK parameters ($AUC_{0-0.04h}$ and $AUC_{0-0.08h}$), statistical analysis showed that early exposure was higher after 5 mg/0.5 mL (Test) group compared to 2 mg/2 mL (Reference), with test-to-reference ratios for $AUC_{0-0.04h}$ of 260.73% (CI: 151.68%, 448.18%) and $AUC_{0-0.04h}$ of 406.26% (CI: 288.61%, 571.89%). These results are in agreement with the study rationale that indicated higher doses of intramuscular naloxone HCl can result in higher $C_{max}$ and more rapid AUCs and these pharmacokinetic characteristics are desirable for a product intended to reverse overdose reactions caused by the higher potency of abused opioid analogues.

The intramuscular injection of naloxone HCl was well-tolerated when administered as either the 5 mg/0.5 mL or 2 mg/2 mL (1 mg/1 mL, International Medical Systems) formulation.

The plasma concentration versus time profiles for both the 5 mg/0.5 mL (Test) and 2 mg/2 mL (Reference) formulations were characterized by rapid absorption, with a higher arithmetic mean $C_{max}$ (SD) being attained after 5 mg/0.5 mL (Test) group (17.2 [7.57] ng/mL) compared to 2 mg/2 mL (Reference) (3.58 [2.08] ng/mL).

Statistical analysis showed that administration of a higher dose of intramuscular naloxone hydrochloride (5 mg/0.5 mL [Test] compared to 2 mg/2 mL [Reference]) resulted in higher $C_{max}$ and AUCs. Statistical analysis also demonstrated that the higher dose of naloxone (test) had a significantly greater AUC during the first 2.5 and 5 minutes compared to Reference.

No significant difference in $T_{max}$ was noted, with a median $T_{max}$ of 0.25 hours reported for both treatments. A significant difference in $t_{1/2}$ was observed, with median $t_{1/2}$ of 1.48 hours and 1.79 hours for 5 mg/0.5 mL (Test) and 2 mg/2 mL (Reference), respectively.

These results show that a higher dose of intramuscular naloxone HCl resulted in higher $C_{max}$ and AUCs and these pharmacokinetic characteristics are desirable for a product intended to reverse overdose reactions caused by the higher potency of abused opioid analogues.

Example 9

Few studies have examined the appropriate dose of naloxone in studies after exposure to opioids. One study examined the effects of i.m. naloxone 6 hours after a single i.m. injection of morphine (18 or 30 mg/70 kg) in six subjects with a history of chronic opiate use. The degree of reversal of the morphine effects was dose related up to 10 mg naloxone intra-muscular for a 70 kg subject with no additional reversal at the 30 mg dose. Withdrawal symptoms were also dose related up to the 30 mg dose. However, withdrawal symptoms were not significantly different from baseline below the 10 mg dose. Similarly, a separate study examined 1, 5, and 10 mg of naloxone intravenously in its ability to reverse buprenorphine intravenous induced respiratory depression in a single blind study. Buprenorphine is a partial opioid receptor agonist. Complete reversal of opioid effects was noted at the 5 mg and 10 mg doses.

Example 10

A 30 year old female is admitted to a local emergency room suffering from an opioid overdose. A high dose naloxone composition is administered by injection to the female. The dose of naloxone was 5 mg in a single injection. The woman recovers from the overdose event.

Example 11

A 30 year old female is admitted to a local emergency room suffering from an opioid overdose. A high dose naloxone composition is administered by injection to the female. The dose of naloxone was 10 mg in a single injection. The woman recovers from the overdose event.

Example 12

A 22 year old male is admitted to a local emergency room suffering from an opioid overdose. A high dose naloxone composition is administered by injection to the male. The dose of naloxone was 20 mg in a single injection. The man recovers from the overdose event.

Example 13

An intramuscular naloxone dose of 5 mg/0.5 mL for the treatment of opioid overdose is proposed. To evaluate the potential local tolerance of naloxone following intramuscular injection, a GLP study was conducted in New Zealand White Rabbits. In order to simulate how the proposed naloxone dose (5 mg/0.5 mL) can be potentially used, we examined a study where three intramuscular injections of naloxone at 5 mg/0.5 mL (15 mg total dose) were compared to three intramuscular injections of the current approved dose of naloxone, at 2 mg/0.4 mL (total dose 6 mg).

Two groups each of 3 male and 3 female rabbits received a single intramuscular injection in 3 sites, located on the left quadriceps femoris muscle, each 5 mg/0.5 mL of naloxone (total dose of 15 mg of naloxone) followed by a 7-day observation period. In addition, one group of 1 male and 2 female rabbits received a single intramuscular injection in 3 sites each of 2 mg/0.4 mL of Naloxone (total dose of 6 mg of naloxone) also followed by a 7-day observation period. Mortality and clinical observations were recorded twice daily. The site of injection was observed for any changes pre-dose, 4 h after dosing, and twice daily thereafter. On Day 8, the animals were euthanized and subject to a necropsy examination. A full tissue list was preserved, but only the test site and contralateral site in the other quadriceps femoris were processed for histopathological evaluation. There were no injection site findings attributed to treatment.

There was a low incidence of slight erythema seen in males receiving 15 mg/animal and females receiving 0 mg/animal. This was attributed to the shaving procedure performed prior to dosing. Histology revealed no evidence that administration of naloxone 5 mg/0.5 mL three times (15 mg total dose) or any of the control test material had any effect on the examined tissue. The only changes were physical disruption of the muscle by passage of the injecting needle.

Example 14

An independent survey is launched to assess the perceived value of a 5 mg/0.5 mL naloxone product, how it impacts prescribing/usage, and consequently the potential product demand. This was an independent survey of Emergency Room and Pain physicians as well as Emergency Medical Services personnel involved in the health care response to the opiate crisis. The participants included 7 Emergency room physicians, 7 pain management physicians, and 6 emergency medical technicians. The survey included pain management physicians, emergency room physicians (ER), and emergency medical services (EMS) representatives.

The survey respondents were geographically dispersed from around the US, representing 11 states; California, Colorado, Georgia, Illinois, Michigan, Minnesota, North Carolina, New Jersey, New Mexico, New York and Ohio.

Respondents were asked to rate on a scale of 1 to 7 their support for statements. Overall, 65% of respondents had a score of 5 or more and agreed that higher doses of naloxone were needed to treat the synthetic opioids. In addition, 50% of respondents had a score of 5 or more and agreed on the need for a 5 mg naloxone prefilled syringe. This research with a panel of representative stakeholders indicates there is a perceived need to treat opioid overdoses, particularly synthetic opioids, with higher doses of naloxone than currently available.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A kit comprising two naloxone filled syringe devices housed in separate connected cases, and instructions for use wherein each case is configured to hold the naloxone filled syringe device at an angled configuration.

2. The kit of claim 1, wherein each naloxone filled syringe device includes 5 mg of naloxone.

3. The kit of claim 1, wherein each naloxone filled syringe device includes 2.5 mg of naloxone.

4. The kit of claim 1, wherein each naloxone filled syringe device includes 10 mg of naloxone.

5. The kit of claim 1, wherein each naloxone filled syringe device includes 15 mg of naloxone.

6. The kit of claim 1, wherein each naloxone filled syringe is configured for a single administration.

7. The kit of claim 6, wherein the administration is an injection.

8. The kit of claim 1, wherein each naloxone filled syringe includes naloxone at a dose greater than or equal to about 5 mg configured for administration, wherein Cmax is between 10 ng/ml to 20 ng/ml.

9. The kit of claim 8, wherein the Cmax is 15.8 ng/ml.

10. The kit of claim 8, wherein the Cmax is 17.2 ng/ml.

11. The kit of claim 1, wherein each naloxone filled syringe includes naloxone at a dose greater than about 5 mg configured for administration, wherein the AUC0-0.04 h is between 0.01 h*ng/ml and 0.1 h*ng/ml.

12. The kit of claim 11, wherein the AUC0-0.04 h is 0.0129 h*ng/ml.

13. The kit of claim 1, wherein each naloxone filled syringe includes naloxone at a dose greater than or equal to about 5 mg configured for administration, wherein the AUC0-0.08 h is between 0.05 h*ng/ml to 0.2 h*ng/ml.

14. The kit of claim 13, wherein the AUC0-0.08 h is 0.0782 h*ng/ml.

15. The kit of claim 1, wherein each syringe device includes a needle.

* * * * *